(12) United States Patent
Zilberman et al.

(10) Patent No.: US 10,524,805 B2
(45) Date of Patent: Jan. 7, 2020

(54) FLEXIBLE BONE TOOL

(71) Applicant: T.A.G. Medical Devices—Agriculture Cooperative Ltd., Kibbutz Gaaton (IL)

(72) Inventors: Roy Zilberman, Qadarim (IL); Aviram Alfia, Karmiel (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 0 days.

(21) Appl. No.: 16/070,526

(22) PCT Filed: Jan. 17, 2017

(86) PCT No.: PCT/IL2017/050062
§ 371 (c)(1),
(2) Date: Jul. 17, 2018

(87) PCT Pub. No.: WO2017/122215
PCT Pub. Date: Jul. 20, 2017

(65) Prior Publication Data
US 2019/0069908 A1    Mar. 7, 2019

Related U.S. Application Data

(60) Provisional application No. 62/436,255, filed on Dec. 19, 2016, provisional application No. 62/279,815, filed on Jan. 17, 2016.

(51) Int. Cl.
*A61B 17/16* (2006.01)
*A61B 17/17* (2006.01)

(52) U.S. Cl.
CPC ...... *A61B 17/1631* (2013.01); *A61B 17/1642* (2013.01); *A61B 17/1714* (2013.01); *A61B 17/1764* (2013.01)

(58) Field of Classification Search
CPC ............ A61B 17/1631; A61B 17/1642; B25B 23/0014; B25G 1/025
See application file for complete search history.

(56) References Cited

U.S. PATENT DOCUMENTS

| 3,060,972 A | 10/1962 | Sheldon |
| 3,430,662 A | 3/1969 | Guarnaschelli |

(Continued)

FOREIGN PATENT DOCUMENTS

| CA | 2173935 | 1/1997 |
| CN | 1575150 | 2/2005 |

(Continued)

OTHER PUBLICATIONS

International Preliminary Report on Patentability dated Sep. 1, 2016 From the International Bureau of WIPO Re. Application No. PCT/IL2015/050178.

(Continued)

*Primary Examiner* — Andrew Yang

(57) ABSTRACT

A flexible bone tool including a plurality of links pivotly coupled to each other and collectively define a substantially tubular, bendable body coupled (a) at a proximal end to a holding portion and (b) at a distal end to a bone tissue removing element. The plurality of links includes one or more proximal links having an engaging portion, a wall of which comprising a first aperture and one or more distal links comprising a receiving portion, a wall of which comprising one or more second apertures, the receiving portion being sized and fitted to receive the engaging portion such that the first and second apertures are aligned and at least one pin sized and fitted to be received by the aligned first and second apertures and pivotly couple said proximal and distal links.

25 Claims, 29 Drawing Sheets

(56) References Cited

U.S. PATENT DOCUMENTS

| | | | |
|---|---|---|---|
| 4,108,211 | A | 8/1978 | Tanaka |
| 4,328,839 | A | 5/1982 | Lyons et al. |
| 4,362,520 | A | 12/1982 | Perry |
| 4,600,037 | A | 7/1986 | Hatten |
| 4,706,659 | A | 11/1987 | Matthews et al. |
| 5,330,480 | A | 7/1994 | Meloul et al. |
| 5,499,984 | A | 3/1996 | Steiner et al. |
| 5,797,918 | A | 8/1998 | McGuire et al. |
| 5,807,241 | A | 9/1998 | Heimberger et al. |
| 6,053,922 | A | 4/2000 | Krause et al. |
| 6,447,518 | B1 | 9/2002 | Krause et al. |
| 7,585,300 | B2 * | 9/2009 | Cha ............... A61B 17/1633 606/80 |
| 7,993,348 | B2 * | 8/2011 | Conte ............. A61B 17/1617 606/79 |
| 8,382,742 | B2 | 2/2013 | Hermann et al. |
| 2002/0171208 | A1 | 11/2002 | Lechot et al. |
| 2004/0044270 | A1 | 3/2004 | Barry |
| 2004/0249367 | A1 | 12/2004 | Saadat et al. |
| 2006/0058582 | A1 | 3/2006 | Maahs et al. |
| 2009/0187244 | A1 | 7/2009 | Dross |
| 2010/0151161 | A1 | 6/2010 | Da Rolo |
| 2010/0287755 | A1 | 11/2010 | Korner |
| 2012/0065638 | A1 | 3/2012 | Moore |
| 2012/0238952 | A1 | 9/2012 | Mitchell et al. |
| 2013/0090690 | A1 | 4/2013 | Walsh |
| 2013/0165908 | A1 | 6/2013 | Purdy et al. |
| 2016/0345986 | A1 | 12/2016 | Slobitker et al. |

FOREIGN PATENT DOCUMENTS

| | | |
|---|---|---|
| EP | 0444776 | 9/1991 |
| JP | 2011-509749 | 3/2011 |
| WO | WO 2015/121869 | 8/2015 |
| WO | WO 2017/122215 | 7/2017 |

OTHER PUBLICATIONS

International Search Report and the Written Opinion dated May 5, 2017 From the International Searching Authority Re. Application No. PCT/IL2017/050062. (11 Pages).

International Search Report and the Written Opinion dated Jul. 7, 2015 From the International Searching Authority Re. Application No. PCT/IL2015/050178.

Notification of Office Action and Search Report dated Dec. 11, 2017 From the State Intellectual Property Office of the People's Republic of China Re. Application No. 201580008925.3. (6 Pages).

Restriction Official Action dated Apr. 6, 2017 From the US Patent and Trademark Office Re. U.S. Appl. No. 15/115,678. (8 pages).

Restriction Official Action dated Jun. 27, 2017 From the US Patent and Trademark Office Re. U.S. Appl. No. 15/115,678. (8 pages).

Supplementary European Search Report and the European Search Opinion dated Nov. 24, 2017 From the European Patent Office Re. Application No. 15749368.5. (6 Pages).

Translation of Notification of Office Action and Search Report dated Dec. 11, 2017 From the State Intellectual Property Office of the People's Republic of China Re. Application No. 201580008925.3. (6 Pages).

International Preliminary Report on Patentability dated Jul. 26, 2018 From the International Bureau of WIPO Re. Application No. PCT/IL2017/050062. (6 Pages).

Notification of Office Action and Search Report dated Jul. 30, 2018 From the State Intellectual Property Office of the People's Republic of China Re. Application No. 201580008925.3. (5 Pages).

Translation Dated Aug. 23, 2018 of Notification of Office Action and Search Report dated Jul. 30, 2018 From the State Intellectual Property Office of the People's Republic of China Re. Application No. 201580008925.3. (6 Pages).

Notice of Reasons for Rejection dated Dec. 12, 2018 From the Japan Patent Office Re. Application No. 2016-548368. (3 Pages).

Translation of Reason for Rejection dated Feb. 5, 2019 of OA of Dec. 12, 2018 From the Japanese Patent Office Re. Application No. 2016-548368. (4 Pages).

* cited by examiner

FLEXIBLE BONE TOOL

RELATED APPLICATIONS

This application is a National Phase of PCT Patent Application No. PCT/IL2017/050062 having International filing date of Jan. 17, 2017, which claims the benefit of priority under 35 USC § 119(e) of U.S. Provisional Patent Application Nos. 62/279,815 filed on and Jan. 17, 2016 and 62/436,255 filed on Dec. 19, 2016. The contents of which the above applications are all incorporated by reference as if fully set forth herein in their entirety.

PCT Patent Application No. PCT/IL2017/050062 also incorporates by reference PCT Patent Application PCT/IL2015/050178 filed on Feb. 17, 2015, the contents of which are incorporated herein by reference in their entirety.

FIELD AND BACKGROUND OF THE INVENTION

The present invention, in some embodiments thereof, relates to a flexible bone tool and, more particularly, but not exclusively, to a flexible bone tool configured to be advanced into a bone in an arthroscopic procedure.

U.S. Pat. No. 6,447,518 B1 discloses: "An improved flexible shaft used in the reaming of the medullary space in bones is described. The shaft is comprised of a solid element with a longitudinal bore the entire length and an appropriately formed slot which extends spirally around the shaft either continuously or segmentally. Attached to the shaft's opposite ends respectively, are a cutting head and a means of connecting the shaft to a driving mechanism. Additionally, an improved anthropomorphic spinal element and vertebral body replacement implant are described. The anthropomorphic spinal element is composed of a solid element with a longitudinal bore and an appropriately formed slot that extends spirally around the shaft either continuously or segmentally and is completely or partially filled with an elastomeric material. The vertebral body replacement implant is composed of a suitable implant material with a longitudinal bore the entire length and an appropriately formed slot which extends spirally around the shaft either continuously or segmentally. Attached to the central section's opposite ends are a means of attachment to the adjacent vertebra allowing for height and angular adjustment."

U.S. Pat. No. 4,362,520A discloses: "This invention is a heavy-duty flexible shaft that accommodates for misalignments between an input and output shaft. The flexible shaft is comprised of a multiplicity of hollow, individually fabricated, interfitting members housed in a tubular, bendable shaft. Each segment is intimately engaged, one within the other, yet the segments are so designed to allow for limited longitudinal movement while restricting circumferential movement between segments during torsional transmissions from the input to the output shafts."

SUMMARY OF THE INVENTION

According to an aspect of some embodiments of the invention, there is provided a flexible bone tool comprising a bone tissue removal element configured at a distal end of the tool; at least two links coupled proximally to the bone tissue removal element, the links connected to each other by a radial interference connection in which at least one radially outwards extending protrusion of a first link is received within a recess of a subsequent link.

According to some embodiments of the invention, each of the links comprises an engaging portion and a receiving portion, the engaging portion positioned distally relative to the receiving portion.

According to some embodiments of the invention, the receiving portion comprises an inner lumen open at a proximal end of the link and leading to the recess, the recess being large enough to receive the at least one protrusion without compressing it inwardly.

According to some embodiments of the invention, the connection is a snap-fit connection in which the at least one radial protrusion is compressed inwardly by the inner lumen of the subsequent link and advanced distally until the protrusion is allowed to elastically snap into the recess, interlocking the first link and the subsequent link to each other while allowing bending of the links relative to each other.

According to some embodiments of the invention, the first link and the subsequent link comprise matching geometries suitable for transferring torque between the links at a magnitude sufficient for advancing the bone tissue removal element into a bone.

According to some embodiments of the invention, the matching geometries comprise at least one surface shaped to interfere with axial rotation of the links relative to each other.

According to some embodiments of the invention, the matching geometries comprise mutual flat faces that contact each other at least one part, wherein a first flat face is configured on the engaging portion of the first link, and a second flat face is configured within the inner lumen of the receiving portion of the subsequent link.

According to some embodiments of the invention, the magnitude of torque ranges between 3 N*cm to 30 N*cm.

According to some embodiments of the invention, the first link and the subsequent link each comprise a receiving recess, wherein the recesses of both links have substantially the same design and are configured to be rotationally oriented relative to each other such that the receiving recess of the first link is configured at an angle to the receiving recess of the subsequent link.

According to some embodiments of the invention, the angle is 90 degrees.

According to some embodiments of the invention, a volume of the at least one radial protrusion occupies no more than 95% of a volume of the recess.

According to some embodiments of the invention, the recess does not extend beyond an outer edge of the receiving portion and the protrusion is internally received within the receiving portion.

According to some embodiments of the invention, the recess extends through an outer edge of the receiving portion and the protrusion is long enough to extend through the recess.

According to some embodiments of the invention, the engaging portion comprises at least one tooth like extension/pin extending in a distal direction, and wherein the protrusion extends radially outwards from the tooth like extension/pin.

According to some embodiments of the invention, the links define a tubular body.

According to some embodiments of the invention, the tubular body is configured to bend into a bending radius of 30 mm or higher.

According to some embodiments of the invention, the tool is cannulated, and wherein the cannulation is shaped and sized to allow delivery of the tool over a guide wire.

According to some embodiments of the invention, the bone tissue removal element is shaped and sized to form a bore in the bone.

According to some embodiments of the invention, the bone tissue removal element is shaped and sized to ream an existing bore in the bone.

According to some embodiments of the invention, the tool further comprises a holding portion at proximal end of the tool, the holding portion engageable by a user or a tool.

According to some embodiments of the invention, the tool is a drill.

According to an aspect of some embodiments of the invention, there is provided a method of advancing a flexible bone tool into a bone, comprising providing a flexible bone tool comprising a plurality of links interlocked to each other by a radial interference connection; introducing the flexible bone tool over a guide wire to approach the bone; rotating the tool to advance at least a distal end of the tool into the bone.

According to some embodiments of the invention, the links are rigid, and wherein the introducing comprises advancing the tool along a curved path defined by the guide wire such that the rigid links bend relative to each other.

According to some embodiments of the invention, an axial gap between adjacent links of the plurality of links is reduced upon contacting the bone.

According to some embodiments of the invention, the advancing comprises forming a bore in the bone.

According to some embodiments of the invention, the advancing comprises reaming an existing bore in the bone.

According to some embodiments of the invention, the bone is the femur and the rotating reams a tunnel in the femur for receiving a graft.

According to some embodiments of the invention, the rotating comprises coupling a drill to a proximal end of the bone tool.

According to an aspect of some embodiments of the invention, there is provided a flexible bone tool comprising a bone tissue removal element configured at a distal end of the tool; at least two links coupled proximally to the bone tissue removal element, the links interconnected to each other by a snap-fit connection in which a first link comprises at least one protrusion which is compressed inwards by an inner lumen of a subsequent link until the at least one protrusion is allowed to elastically snap into a respective recess of the subsequent link that the inner lumen leads to.

According to some embodiments of the invention, the inner lumen is open at a proximal end of the subsequent link and extends longitudinally within a receiving portion of the subsequent link, the inner lumen shaped and sized to compress the at least one protrusion radially inwards.

According to some embodiments of the invention, the snap-fit connection interlocks the first link and the subsequent link to each other while allowing bending of the links relative to each other.

According to an aspect of some embodiments of the invention, there is provided a kit for adjusting a flexible bone tool, comprising a plurality of interconnectable links, the links configured to engage each other by a snap-fit connection to form an elongated, bendable body.

According to some embodiments of the invention, the tool comprises a proximal holding portion and wherein at least one of the links is configured to engage the proximal holding portion.

According to some embodiments of the invention, the kit further comprises a plurality of cutting heads out of which one cutting head is selected, the cutting head configured to engage a distal end of at least one of the links.

According to an aspect of some embodiments of the invention, there is provided a method of adjusting a flexible bone tool, comprising: providing a flexible bone tool comprising a plurality of links interconnected to each other by a snap-fit connection; attaching or removing one or more links to adjust a length of the bone tool.

According to some embodiments of the invention, the method further comprises selecting a cutting head of a certain shape or size and connecting the cutting head to a most distal link of the plurality of links.

According to some embodiments of the invention, the attaching or removing provides at least one of audible, sensible or visible feedback to the user.

According to some embodiments of the invention, the audible feedback comprises a "click" type sound when the links interlock to each other.

According to an aspect of some embodiments of the invention, there is provided a flexible bone tool comprising a bone tissue removal element configured at a distal end of the tool; at least two links coupled proximally to the bone tissue removal element, the links interconnected to each other by a "click" type connection in which a sound indication is provided in the process of connecting the links.

According to an aspect of some embodiments there is provided a flexible reamer slidable over a guide pin, comprising:
  a proximal holding portion;
  an intermediate portion;
  a distal portion including a plurality of interconnected links, attached in an articulated manner, which allows force transfer from one link to a subsequent link in a direction corresponding to the direction of the guide pin.

In some embodiments, the flexible reamer also comprises a distal drilling end.

In some embodiments, the guide pin is made of Nitinol.

In some embodiments, the links are inseparably interconnected.

In some embodiments, the links are interconnected by a snap-fit.

In some embodiments, a fulcrum point of said distal portion is formed at a most-proximal link.

According to an aspect of some embodiments of the invention there is thus provided a flexible bone tool including a holding portion, a bone tissue removing element and a plurality of links pivotably coupled to each other and collectively define a, bendable body; the plurality of links coupled a) at a proximal end to the holding portion; and b) at a distal end to the bone tissue removing element, wherein the plurality of links includes at least 2 links, each link having an engaging portion, a wall of which includes at least a first aperture and a receiving portion, a wall of which includes at least one second aperture, the receiving portion sized and fitted to receive the engaging portion such that the first and second apertures are aligned and at least one pin sized and fitted to be received by the aligned first and second apertures and pivotably couple the proximal and distal links.

In some embodiments of the invention the flexible bone tool links include an engaging portion and a receiving portion each including at least one aperture. In some embodiments, the links include an engaging portion and a receiving portion each including at least one pair of diametrically opposed apertures wherein a first imaginary line connecting a pair of diametrically opposed apertures in a receiving portion is at an angle in respect to a second imaginary line connecting diametrically opposed apertures in the engaging portion. In some embodiments, the angle is 90 degrees.

In some embodiments of the invention the invention a first imaginary line connecting a pair of diametrically opposed apertures in a receiving portion of a distal link is at an angle in respect to a second imaginary line diametrically opposed apertures in a receiving portion of a preceding or following subsequent links. In some embodiments, the angle is 90 degrees.

According to some embodiments of the invention at least one link is operative to pivot 2-10 degrees in respect to at least one of a preceding or following subsequent links. In some embodiments, the tool includes a plurality of links and configured to bend in a bending radius R between 20 and 80 mm. In some embodiments, the tool includes a plurality of links and configured to follow a generally L-shaped curve. In some embodiments, the tool includes a plurality of links and configured to follow a generally U-shaped curve. In some embodiments, the tool includes a plurality of links and is configured to bend at an angle between 0 and 180 degrees in respect to the rotational axis of the holding portion. In some embodiments, a degree of pivot accumulated along said plurality of links defines a bending radius of said tool.

According to an aspect of some embodiments of the invention there is thus provided a flexible bone tool including wherein matching geometries of the engaging portion and a corresponding inner lumen of a consecutive receiving portion are suitable when engaged for transferring torque between the links at a magnitude sufficient for advancing the bone tissue removal element into a bone. In some embodiments, subsequent links include matching geometries suitable for transferring torque in a range between ranges between 3 N*cm to 30 N*cm between the links. In some embodiments, matching geometries of the engaging portion and a corresponding inner lumen of a consecutive receiving portion allow axial rotation of the links relative to each other only to an extent in which sufficient torque can still be transferred between the links.

According to an aspect of some embodiments of the invention there is thus provided a flexible bone tool including a bone removal element is shaped and sized to at least one of cut bone, form a bore in the bone and ream an existing bore in the bone and at least a portion of the flexible tool is slidable over at least one of a guide pin and a guide wire. In some embodiments, the coupling includes a radial interference coupling.

According to some embodiments of the invention, at least one of the tubular body and proximal holding portion is cannulated. In some embodiments, at least one of the pins includes a cylindrical portion and an outwardly tapered portion defining an outwardly facing surface and at least one of the pins includes a cylindrical portion and a pin head having a flat surface that abuts an inside wall surface facing a lumen of the links. In some embodiments, at least one of the pins includes a cylindrical portion and a pin head tapered radially inwardly so that to fit in a recess around a circumference of the aperture in an inside wall surface of the links and at least one of the apertures is formed within a circumferential recess on an outer surface of the receiving portion.

According to an aspect of some embodiments of the invention there is thus provided a flexible bone tool including a fixator having annular geometry. In some embodiments, the fixator has semi-circular geometry. In some embodiments, the fixator is resilient and defines an inwardly facing surface, an outwardly facing surface and a slit, which enables the fixation element to deform resiliently upon application of stress. In some embodiments, the fixator has notional dome geometry including a plurality of mutually separated finger-like projections.

According to some embodiments, an outer surface of the receiving portion includes a circumferential recess, the pins received by apertures formed in the recess and the fixator lies along the circumferential recess with the inwardly facing surface engaging an outwardly facing surface of at least one of the pins received in the apertures and the fixator includes diametrically opposed fixedly attached pins.

According to an aspect of some embodiments of the invention there is thus provided a flexible bone tool including bendable body having a bending radius defined by the number of links including the body. In some embodiments, the bending radius of the bendable body is defined by at least one dimension of the links selected from a group of dimensions including: outer diameter of engaging portion of links, length of engaging portion of links, inner diameter of receiving portion of link. In some embodiments, the tubular body includes a flexible core.

According to some embodiments, at least one of the apertures is axially oblong so that the flexible tool includes at least one axial gap between at least two subsequent links that reduces upon contacting bone. In some embodiments, the links are rotated about their longitudinal axis in respect to each other, e.g., the links are rotated 90 degrees in respect to each other. In some embodiments, the bone tissue removing element is replaceable.

According to an aspect of some embodiments of the invention there is thus provided a method of drilling a curved bore in bone including introducing a least a portion of a guide wire into bone, sliding a flexible bone tool including a bone cutting head over the guide wire and up against the bone, rotating the tool to advance at least a distal end of the tool into the bone; and advancing the tool along a curved path defined by the guide wire. The method further includes removing the flexible bone tool, detaching the cutting head and replacing the cutting head with a reamer head, sliding the flexible bone tool over the guide wire and into a drilled bore in the bone and reaming the bore.

According to an aspect of some embodiments of the invention there is thus provided a kit for drilling a curved bore in bone including at least one flexible bone tool including at least one proximal holding portion, at least one first link attachable distally to the holding portion, at least one second link including a tissue removing element attachable to at least one of the holding portion and the first link, a plurality of connecting pins and at least one link detachment tool. In some embodiments, tissue removing element is configured to at least cut bone, form a bore in the bone and ream an existing bore in the bone. In some embodiments, the link detachment tool is configured to detach links and/or the link including a tissue removing element and the initial base length is in a range between 30-120 mm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 27A and 27B, in which FIG. 27A is a plan view and side view simplified illustration of a link detachment tool in accordance with some embodiments of the invention and FIG. 27B is a side view simplified illustration of implementation of the link detachment tool depicted in FIG. 27A.

DESCRIPTION OF SPECIFIC EMBODIMENTS OF THE INVENTION

Figure 1:
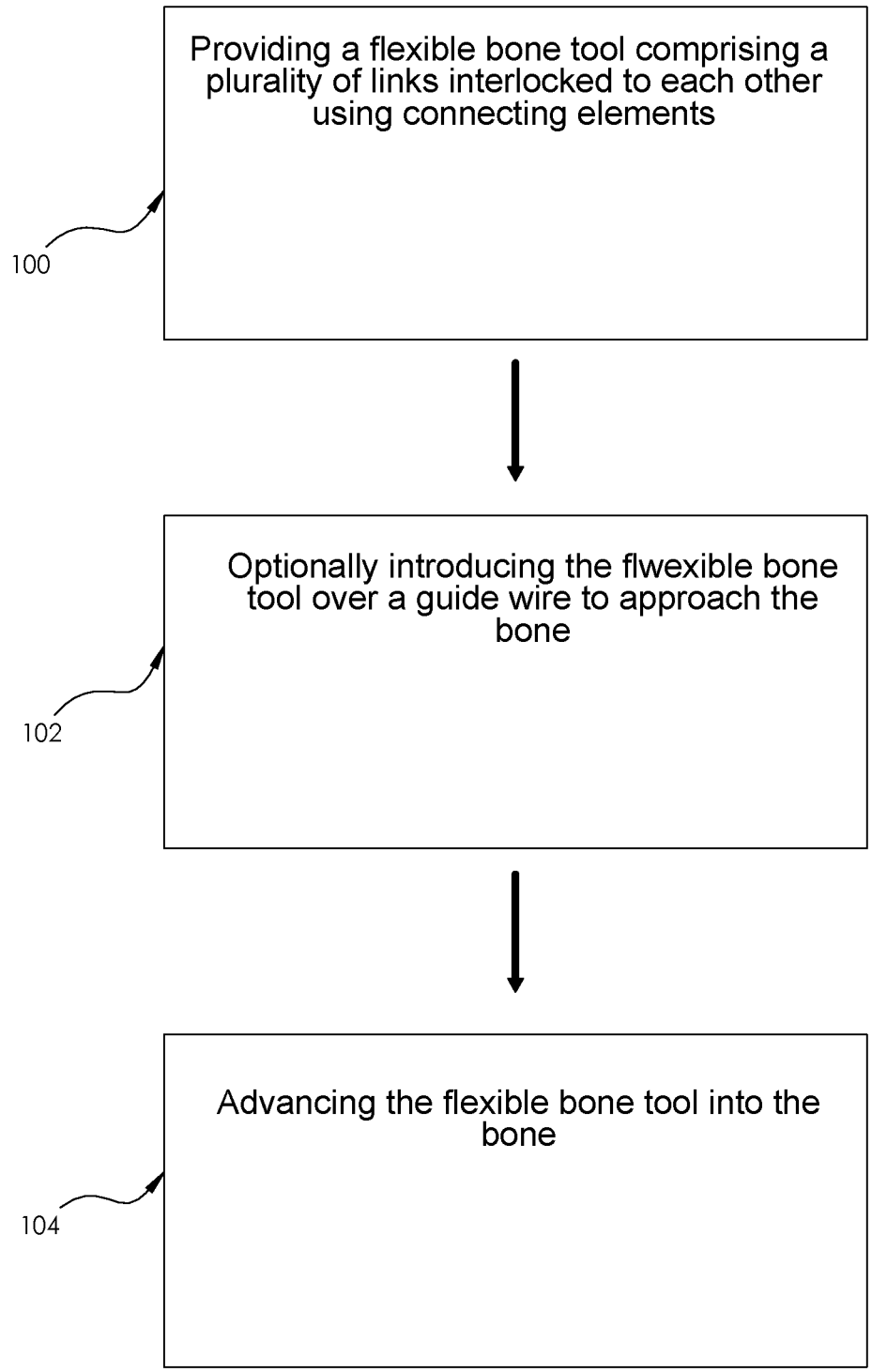
FIG. 1 is a flowchart of a method of advancing a flexible bone tool comprising a plurality of links interlocked by a snap fit connection into a bone, according to some embodiments of the invention.

The present invention, in some embodiments thereof, relates to a flexible bone tool and, more particularly, but not exclusively, to a flexible bone tool configured to be advanced into a bone in an arthroscopic procedure in bone drilling or in orthobiological procedures.

An aspect of some embodiments of the invention relates to a flexible bone tool comprising a plurality of links interconnected to each other by a radial interference connection. In some embodiments, the links are arranged along a common axis to form an elongated body. In some embodiments, the elongated body has tubular geometry. In some embodiments, the tubular body comprises between 10 and 50 links. In some embodiments, the tubular body comprises between 20 and 40 links, less than 10, more than 50 or any intermediate number.

In some embodiments, an outer diameter of the tubular body ranges between, for example, 2-10 mm, 4-6.5 mm, 5-20 mm, or intermediate, larger or smaller diameters. In some embodiments, the flexible tubular body length ranges between 30-120 mm, 40 mm-100 mm, 60-80 mm, longer than 120 mkm, shorter that 30 mm or any intermediate length. In some embodiments, embodiments, the diameter of a single link is between 2-6.5 mm, 3-4.5 mm, less than 3 mm, more than 6.5 mm or any intermediate diameter. In some embodiments, the length of a single link is between 2-8 mm, 4-6 mm, less than 2 mm, more than 8 mm or any intermediate length.

In some embodiments, the length of a link is defined by at least one of outer dimension (e.g., diameter) of engaging portion of previous link, thickness of wall of link receiving portion (i.e., inner diameter of the receiving portion) and axial gap between two coupled links.

In some embodiments, the radial interference connection comprises pins inserted through apertures in walls of the links. In some embodiments, the pins are inserted via aligned apertures of a first link and apertures of a second preceding or consecutive link. In some embodiments, the pins are cylindrical. In some embodiments, the pins are inserted under pressure and held inside the apertures by friction. In some embodiments, the pins comprise pin heads on one end that abut an inside wall surface facing a lumen of at least one link and prevent the pins from falling out of place under centrifugal or other forces applied when the tool is rotated.

In some embodiments, the pin head comprises a flattened surface that abuts inside wall surface facing a lumen of one or more links. In some embodiments the pin head is tapered radially inwardly so that to fit in a recess around a circumference of a receiving aperture in an inside wall surface facing a lumen of one or more links.

An aspect of some embodiments of the invention relates to flexible bone tool comprising a plurality of links. In some embodiments, links comprising at least a portion of the bone tool are similar to each other. In some embodiments, the links are dissimilar to each other. In some embodiments, the links comprise different lengths. In some embodiments, the links comprise different diameters. In some embodiments, an angle of pivot between links varies along the length of the flexible tubular body. In some embodiments, the pins allows for at least pivotal movement of coupled links in respect to one another while maintaining the coupled links in an interlocked configuration. In some embodiments, the links comprise similar and dissimilar links. In some embodiments, each link comprises at least one receiving portion and at least one engaging portion. In some embodiments, the receiving portion of a first link is sized and fitted to receive the engaging portion of a second link. In some embodiments, the engaging portion of a first link is sized and fitted to be inserted in the receiving portion of a second link.

In some embodiments, the flexible tubular body comprises rotational symmetry. In some embodiments, the flexible tubular body comprises rotational asymmetry. In some embodiments, the links are made of a hard material suitable for withstanding and transferring torque along the body of the link and between the links at a magnitude sufficient for advancing the bone tissue removal element into a bone.

In some embodiments, each of the receiving portion and the engaging portion comprises diametrically opposed radially facing apertures. In some embodiments, a first imaginary line connecting a pair of diametrically opposed apertures in a receiving portion is at an angle in respect to a second imaginary line connecting diametrically opposed apertures in the engaging portion. In some embodiments, the angle is 90 degrees. In some embodiments, the apertures extend the full thickness of the link wall. In some embodiments, the apertures are sized and fitted to receive at least one pin. In some embodiments, the length of the pin is at least two link wall thicknesses measured at the level of the apertures.

In some embodiments, at least a portion of the flexible bone tool comprises at least one first proximal link and at least one second subsequent distal link. In some embodiments, an engaging portion of the proximal link is moveably received inside a receiving portion of the distal link. In some embodiments, the proximal and distal links are engaged such that the apertures in the engaging portion of the proximal link aligned with the apertures in the receiving portion of the distal link.

In some embodiments, the links are connected by a radial interference connection. In some embodiments, the radial interference connection comprises at least one pin received by both aligned apertures of the engaging portion of the proximal link and the receiving portion of the distal link and extends in a radial direction relative to a longitudinal axis of the elongated body and received in the apertures of the first link and a second subsequent link.

In some embodiments, the connection between the links provides for movement of the links relative to each other. In some embodiments, the movement is a pendulous movement. In some procedures, it may be necessary to access the bone by following a curved path, (i.e. rather than directly accessing the bone), for example due the anatomy of the treated area. In some procedures, the targeted bone is approached at a certain angle. A flexible tool as described herein may be particularly useful in such procedures, owing to the articulation ability of the tubular body. In some embodiments, the articulation ability between adjacent links enables the advancement of the tool along a curved path, such as when approaching the bone through the soft tissue and/or when advancing into the bone.

In some embodiments, the flexible tool is introduced over a guidewire. Optionally, in some embodiments, the guide wire defines a curved path leading the flexible bone tool to the bone. Alternatively, the guide wire defines a substantially linear path leading to the bone. In some embodiments, the flexible tool can be flexed to closely follow the path defined by the guide wire. Optionally, in some embodiments, the elongated body can be flexed into a bending radius as small as 50 mm, 30 mm, 60 mm or intermediate, larger or smaller radii.

In some embodiments, the radial interference connection is configured to maintain the coupling between the links, for example by resisting pull-out force acting on the tool during retraction from the body.

An aspect of some embodiments of the invention relates to flexible bone tool comprising a plurality of links coupled by pins and a fixator retaining the pins in place. In some embodiments, the fixation device has annular geometry. In some embodiments, the fixator has semi-circular geometry. In some embodiments, the fixator is resilient and defines an inwardly facing surface, an outwardly facing surface and a slit, which enables the fixation element to deform resiliently upon application of stress. In some embodiments, an outer surface of the receiving portion includes a circumferential recess. In some embodiments, the pins are received by apertures formed in the recess and the fixator lies along the circumferential recess with the inwardly facing surface engaging an outwardly facing surface of at least one of the pins. In some embodiments, the fixator includes diametrically opposed fixedly attached pins. In some embodiments, the fixation element comprises a snap-fit attachment to a corresponding link. In some embodiments, the fixator has notional dome geometry including a plurality of mutually separated finger-like projections.

In some embodiments, when applied, the fixator envelopes at least a portion of a link at the level of the circumferential recess and apertures formed within the recess and blocks the pins from radially exiting the apertures.

An aspect of some embodiments of the invention relates to a flexible bone tool comprising a plurality of links interconnected to each other and allow transfer of force one to the other. In some embodiments, the links have a matching geometry structured to allow transferring of force such as torque between the links. In some embodiments, the transferred force comprises a magnitude sufficient for advancing at least a distal end of the tool into bone. In some embodiments, torque is applied to a proximal end of the tool, for example by a drill, and is transferred in a distal direction by the interconnected links. In some embodiments, a cutting head is configured at a distal end of the tool, and torque at a magnitude sufficient for forming a bore in the bone and/or for reaming an existing bore in the bone is transmitted by the links in the distal direction to the cutting head.

In some embodiments, the cutting and/or reaming head is replaceable. In some embodiments, the cutting and/or reaming head size and/or type is selected from a selection of head types and sizes and attached to a distal end of the flexible tubular portion prior to the medical procedure. In some embodiments, the cutting and/or reaming head is detached employing a link detachment tool.

In some embodiments, the matching geometry of the links includes at least one surface shaped to interfere with axial rotation of a link relative to the adjacent link. In some embodiments, adjacent links are angularly rotated relative to each other. Optionally, apertures of a receiving link are positioned at an angle relative to the apertures of the subsequent link, for example a 90 degree angle.

In some embodiments, the flexible bone tool may be configured to be disposable following use during single surgical procedure. An aspect of some embodiments of the invention relates to flexible bone tool comprising a bone tissue removal element at a distal end of the tool. In some embodiments, the bone tissue removal element is configured for forming a bore in the bone. In some embodiments, the bone tissue removal element is configured for reaming an existing bore in the bone. In some embodiments, the bone tissue removal element is configured for forming a bore in the bone and/or reaming an existing bore in the bone.

In some embodiments, a specific cutting head e.g., of a certain shape and/or size and/or function (e.g. a head configured for drilling, a head configured for reaming) is selected and attached at a distal end of the tool, for example connected to the most distal link.

An aspect of some embodiments of the invention relate to a kit comprising one or more flexible bone tools and including one or more proximal holding portions and one or more links attached distally to the holding portion; a plurality of separate links for adding to the tool; and/or a plurality of cutting heads of various shapes and/or sizes and/or functions. In some embodiments, the kit may include an adjustment device configured to assemble the links and/or to detach the links and/or to assemble, replace or detach the cutting head.

In some embodiments of the invention, a "bone tissue removal element" and/or "cutting head" refer to an element shaped and sized for one or more of cutting bone, forming a bore in the bone, reaming an existing bore in a bone, penetrating bone tissue, fragmenting or crumbling bone tissue and grinding the bone.

As referred to herein, the term "proximal" may refer to a direction of the user end of the tool, such as an outside the body direction; the term "distal" may refer to a direction of the targeted bone, away from the user end of the tool.

In some embodiments, during various arthroscopic procedures and particularly during Anterior Cruciate Ligament Reconstruction (ACL Reconstruction), a surgical tissue graft is inserted into a bore created in the knee in order to replace the injured anterior cruciate ligament. The injured ligament is removed from the knee before the graft is inserted through the bore created by drilling. A possible challenge which may be associated with this technique is approaching the knee joint at a certain angle. Several optional methods have been developed for enabling engagement between the femoral bone and the reamer at a certain angle. An optional exemplary method is to position a drill guide and guide pin through on the femoral bone and slide a reamer over the guide pin in order to create a femoral tunnel.

Some embodiments relate to a flexible surgical reamer, which provides for convenient positioning of the drill against the femoral bone.

Some embodiments of the present invention relate to flexible reamers for use in arthroscopic reconstruction procedures, particularly useful in Anterior Cruciate Ligament Reconstruction (ACL) procedures.

Some embodiments of the invention seek to provide an improved flexible reamer for drilling a tunnel in a human femoral bone.

There is thus provided in accordance with an embodiment of the present invention a flexible reamer slidable over a guide pin. In some embodiments, the reamer includes a proximal holding portion, an intermediate portion, a distal portion including a plurality of interconnected links. Optionally, the links are attached in an articulated manner, which allows force transfer from one link to a subsequent link in a direction corresponding to the direction of the guide pin.

In accordance with an embodiment of the present invention, the flexible reamer also includes a distal drilling end.

Optionally, the guide pin is made of Nitinol.

Further in accordance with an embodiment of the present invention, the links are inseparably interconnected.

In some embodiments, the links are interconnected by a connecting pin.

In some embodiments, the links may be produced using a deep drawing process.

Some embodiments relate to a flexible reamer slidable over a guide pin, including a proximal holding portion, an intermediate portion, a distal portion including a plurality of interconnected links, attached in an articulated manner, which allows force transfer from one link to a subsequent link in a direction corresponding to the direction of the guide pin.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a flowchart of a method for advancing a flexible bone tool comprising a plurality of links interconnected using connecting elements into a bone, according to some embodiments of the invention.

In some embodiments, a flexible bone tool comprising a plurality of links interconnected by connecting elements, for example as further described herein, is provided (100). In some embodiments, the links are arranged along a common longitudinal axis. In some embodiments, the chained links define a substantially tubular, bendable body. In some embodiments, the bone tool comprises a cutting head configured at a distal end of the tubular body. Optionally, the cutting head is shaped and/or sized to cut a bore in the bone, allowing the tool to function as a drill bit. Additionally or alternatively, the cutting head is shaped and/or sized to widen an existing bore in the bone, for example when rotary motion is applied to the tool, for example to a proximal head portion of the tool, allowing the tool to function as a reamer. In some embodiments, the bone tool comprises a holding portion configured proximally to the tubular body. The proximal holding portion may be engaged by a user, such as a physician, and/or by an additional tool, such as a drill. In some embodiments, the tubular body and optionally the proximal holding portion are cannulated. Optionally, the cannulated tool is delivered over a guide wire, guide pin, suture and/or other elongated elements that can fit within and/or be passed through the cannulation.

In some embodiments, a guide wire is introduced to the targeted bone. Optionally, an initial bore is drilled in the bone, for example by advancing the guide wire into the bone, such as with the aid of a drill. In some embodiments, at least a portion of the guide wire is bent into an arch or other curved profile. Optionally, the guide wire is bent into a selected curvature once at least a part of it (e.g. a distal end) has been anchored to the targeted bone.

In some embodiments, the flexible bone tool is introduced over the guide wire (102). Optionally, the guide wire defines a curved path leading the flexible bone tool to the bone. Alternatively, the guide wire defines a substantially linear path leading to the bone. In some procedures, it is necessary or preferable to access the bone by following a curved path, (i.e. rather than directly accessing the bone), for example due the anatomy of the treated area. In some procedures, the targeted bone is approached at a certain angle. A flexible tool as described herein may be particularly useful in such procedures, owing to the articulation ability of the tubular body.

In some embodiments, the flexible bone tool is advanced into the bone (104). In some embodiments, advancing the tool comprises axially rotating the tubular body, for example by coupling a drill to the proximal holding portion of the tool. Optionally, at least a portion of the tubular body of the tool is advanced into a pre-formed bore in the bone, and widens a diameter of the bore upon advancement. Alternatively, the tool produces the bore. In some embodiments, the snap-fit connection between the plurality of links of the tubular body is strong enough to withstand resisting forces of the bone, while allowing transmission of force such as torque between the links, for example from the proximal holding portion to the distal head.

A method for example as described herein may be especially advantageous in arthroscopic procedures, and particularly useful in Anterior Cruciate Ligament Reconstruction procedures, in which a bore is formed in the femoral bone. In some cases, the bone is approached at a certain angle for forming the bore which requires following a curved path that circumvents soft tissue organs or other bones. Optionally, a flexible bone tool in accordance with some embodiments is introduced to the femoral bone, (optionally over a bent guide wire that was used for creating an initial bore in the bone), and functions as a reamer for widening the initial bore to produce a tunnel for receiving a graft. Optionally, the tool is introduced along a curved path to meet the bone at a desired location.

In some embodiments, a user selects a cutting head suitable for performing a desired function (e.g. penetrating a bone to produce a bore, widening an existing bore, and/or other functions), and assembles the head onto the tool.

Figure 2A:
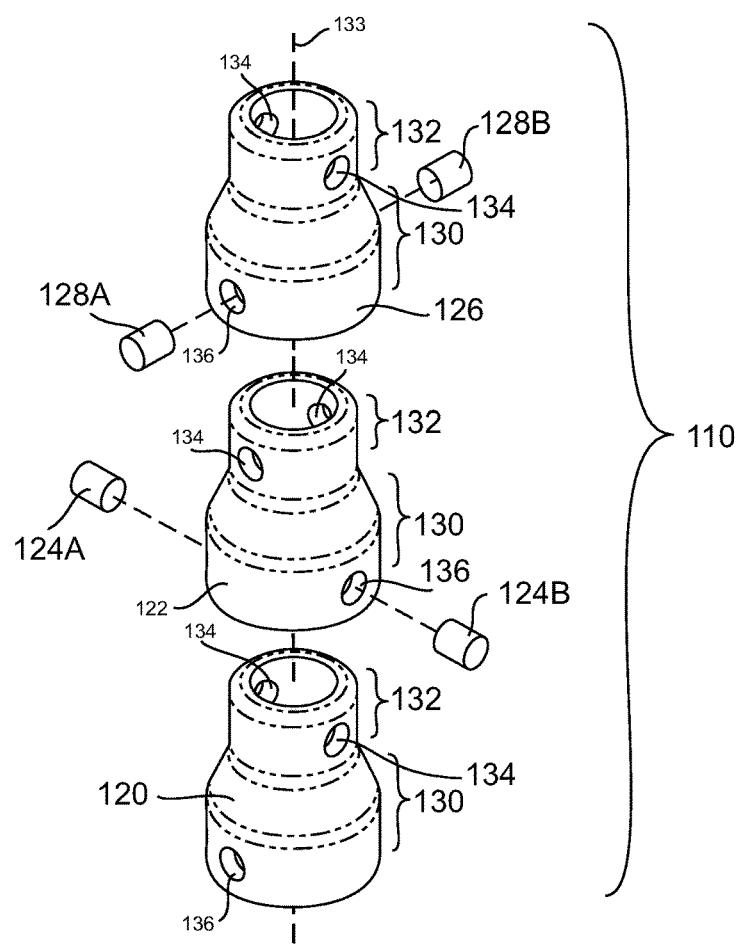
FIGS. 2A, 2B and 2C which are exploded view simplified illustration of a link structure of the flexible bone tool and side view simplified illustration of pin types in accordance with some embodiments of the present invention.
Figures 2B, 2C:
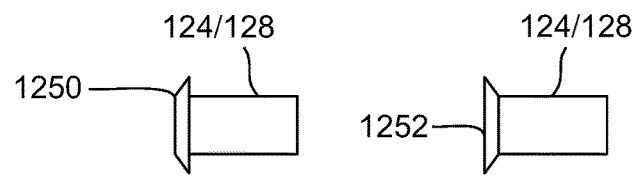

Reference is now made to FIGS. 2A, 2B and 2C, which are exploded view simplified illustration of a link structure of the flexible bone tool and side view simplified illustration of pin types in accordance with some embodiments of the present invention. As shown in FIGS. 2A-C, in some embodiments, each link comprises one or more apertures or one or more pairs of radially diametrically opposed apertures e.g., 134/136 sized and fitted to receive one or more pins e.g., 124A/B and/or 128A/B that comprise a radial interference connection between every two subsequent links. In some embodiments, pins e.g., 124A/B and/or 128A/B are cylindrical and are inserted under pressure and held inside apertures e.g., 134/136 by friction alone. In some embodiments, as shown in FIGS. 2B and 2C pins 124/128 comprise pin heads 250/252 on one end of the pin and abut an inside wall surface facing a lumen of links 120 and prevent the pins from falling out of place under centrifugal or other forces applied when tool 150 is rotated. As shown in FIG. 2B, pin head 1250 comprises a flattened surface that abuts inside wall surface facing a lumen of links 120. In some embodiments and as shown in FIG. 2C, pin head 1252 is tapered radially inwardly so that to fit in a recess around a circumference of aperture 134/136 in an inside wall surface facing a lumen of links 120. In some embodiments, a single pin is threaded via apertures 134 and/or 136. In some embodiments, each pair of pairs of pins e.g., 124A/B and/or 128A/B are threaded via corresponding apertures 136 and/or 134.

In some embodiments and as shown in FIGS. 2A-C, connection of three links 120, 122 and 126 forms a flexible portion 110 of a flexible bone tool. In the depicted embodiment, a first link 120 is configured to be connected to a subsequent, more distal link 122 by means of two connecting pins 124A and 124B and a further distal link 126 connected to link 122 by connecting pins 128A and 128B. In some embodiments, each link 120, 122 and 126 comprises a receiving portion 130 and an engaging portion 132 such that each link (120/122/124) comprises an engaging portion 132 configured to be received within a receiving portion 130 of the subsequent link. E.g., a receiving portion 130 of a second link (e.g., 122) is sized and fitted to receive the engaging portion 132 of a first proximal link (e.g., 120).

In some embodiments, engaging portion 132 comprises cylindrical geometry and comprises at least two diametrically opposed apertures 134. Alternatively and optionally, in some embodiments, engaging portion 132 defines different cross-section circumference geometry, outer profiles, e.g., hexagonal, oval, and/or other outer profile configured to be received within the receiving portion 130 of the subsequent link.

In some embodiments, receiving portion 130 comprises a generally cylindrical first proximal segment and an inwardly tapering second distal segment and two diametrically opposed apertures 136 located in a wall of the first proximal segment of receiving portion 130. In some embodiments, the apertures 136 are circular. In some embodiments, the apertures 136 and/or 134 are axially oblong. Alternatively and optionally, a link (e.g., 122) receiving portion 130 defines a different inner profile, such as hexagonal, oval, and/or other outer profile configured to receive within the corresponding engaging portion 132 of a contiguous proximal link (e.g., 120). In some embodiments, apertures 136 and/or 134 are axially oblong and extend parallel to axis 133. Oblong apertures 136 and/or 134 allow axial movement of one link in relative to a preceding or following consecutive link.

In some embodiments, links 120, 122 and 126 are generally arranged along a mutual longitudinal axis 133 at rest.

In some embodiments, the outer profile of engaging portion 132 of link 120 is of a generally smaller outer diameter than an inner diameter of a receiving portion 130 of subsequent link 122, so as to fit within the receiving portion 130.

In some embodiments, the inner profile of receiving portion 130 is of a generally larger inner diameter than an outer diameter of the engaging portion 132 of the proximal link 120, so as to receive the engaging portion 132 therein. E.g., The engaging portion 132 of a first proximal link (e.g., 120) is sized and fitted to be inserted and fit in the receiving portion 130 of a second subsequent distal link (e.g., 122).

In some embodiments, when the links are axially aligned, link 122, for example is axially rotated at an angle of typically 90 degrees with respect to contiguous proximal link 120, such that apertures 136 of link 122 are aligned with apertures 134 of link 120.

In some embodiments, each link comprises a plurality of apertures 134 and 136 and connecting pins 124 or 128, for example 2, 3, 4, 5, 6, 10 pins or intermediate, larger or smaller number. Optionally, links of a single tool comprise different numbers of extensions/pins. Optionally, the number of extensions/pins determines the extent of movement of the links relative to each other. For example, a single aperture may provide for a higher degree of freedom of movement relative to a larger number of apertures, for example movement in the axial and/or radial directions.

In some embodiments, the links are formed of metal, for example, stainless steel. Additionally or alternatively and optionally, the links are formed of a biocompatible plastic for example, polycarbonate and/or isoplast.

In some embodiments, at least one link and/or at least the tubular body and/or cutting head are disposable.

In some embodiments, the magnitude of torque transferred by the links is sufficient for drilling into the bone tissue, for example, ranging between 3 N*cm-15 N*cm. Optionally, the tubular body is configured to transfer a magnitude of torque ranging between 1 N*cm to 150 N*cm, for example, 5-20 N*cm, 10-40 N*cm, 50-100 N*cm.

In some embodiments, the matching non-circular geometries of the engaging portion and an inner lumen of the receiving portion are sized and fitted to allow axial rotation of the links relative to each other only to an extent in which torque sufficient to maintain functionality of the tool can still be transferred between the links.

Figure 3A:
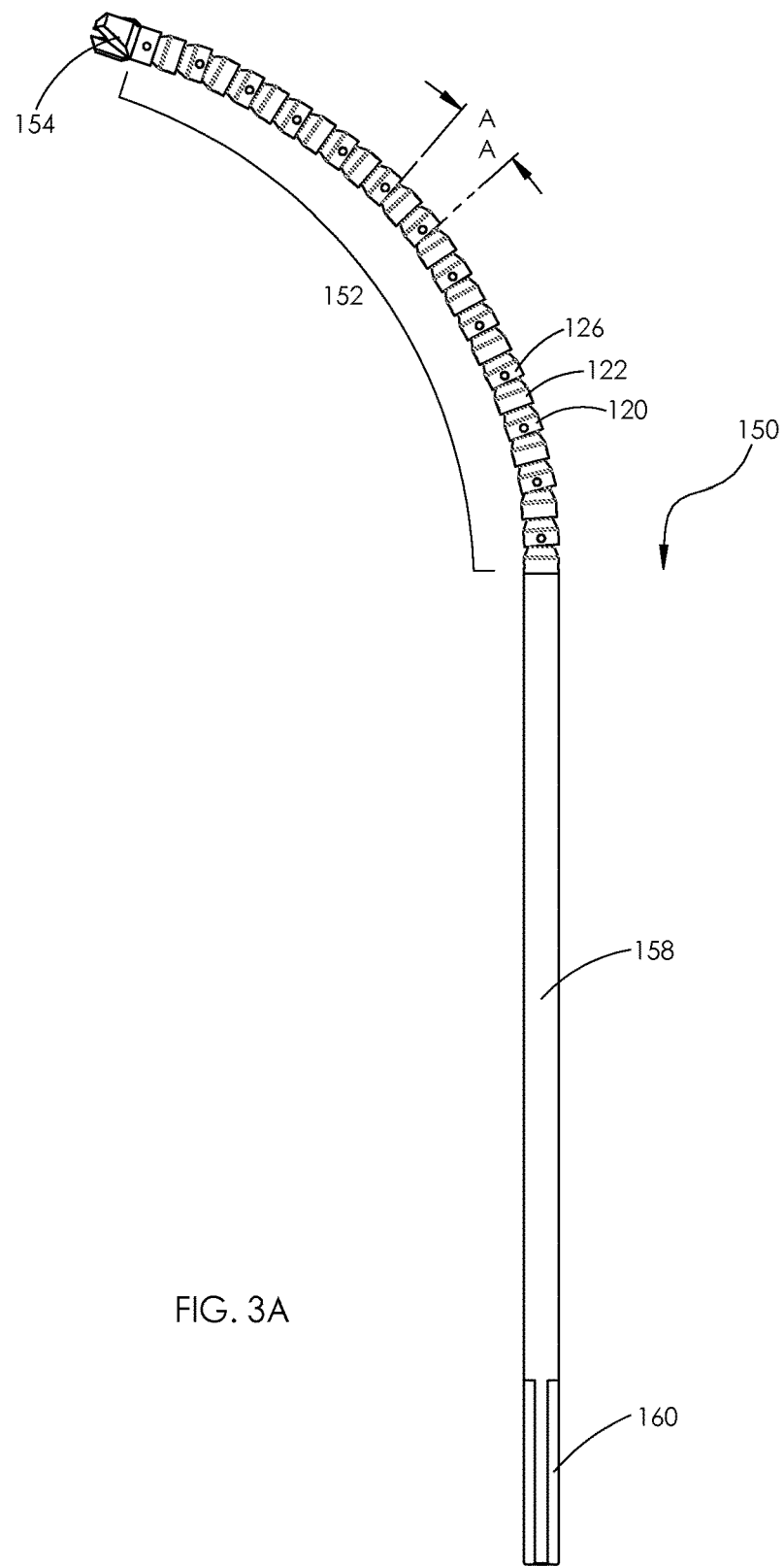
FIGS. 3A and 3B is a side-view simplified illustration of a flexible bone tool in a flexed configuration and straight configuration respectively, according to some embodiments of the invention.
Figure 3B:
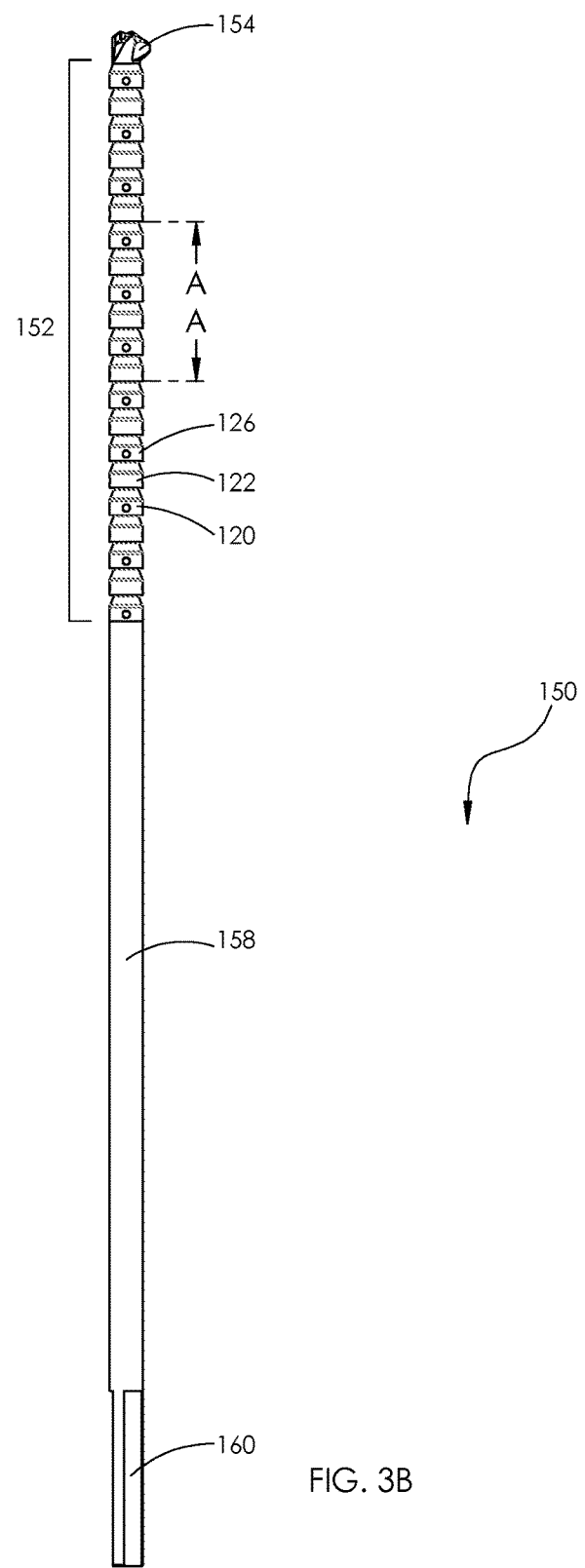

Reference is now made to FIGS. 3A & 3B, which are side-view simplified illustrations of a flexible bone tool in a flexed configuration and straight configuration respectively, according to some embodiments of the invention;

FIG. 3A shows an embodiment of flexible bone tool 150 in a flexed configuration. Tool 150 comprises a tubular body 152 a distal portion of which includes an optional cutting head 154. Optionally, in some embodiments, flexible bone tool 150 can be threaded over a guide wire 156 (not shown) that, when threaded, protrudes from the distal end of the tool 150. Tool 150 comprises a holding portion 158 proximally to the tubular body 152. Holding portion 158 comprises proximally a proximal head portion 160, which is shaped and/or sized to be engaged by a drill and/or other tool.

In some embodiments, tool 150 is structured to follow a path defined by threaded guide wire 156, for example being a curved and/or straight path. In some embodiments, tubular body 152 is configured to bend into a bending radius R. Optionally, bending radius R can be as small as, for example, 50 mm, 30 mm, 20 mm or intermediate, larger or smaller radii.

In some embodiments, the ability of the tubular body to flex to comply with the guide wire curvature is provided by the relative angular orientation between the links 120 and 122 or 122 and 126. Optionally, during application of rotary motion to the tool (e.g. during drilling), the links become re-aligned with the guide wire path every fraction of a turn which is determined by the relative angular orientation between the links. In an example, in a 90 degree orientation between adjacent links, the links would "return" to the defined path every quarter of a turn. Optionally, the rotational orientation of the links reduces a discretization effect during rotation, which may be caused due the rigid links, resulting in a non-continuous rotation. Optionally, reducing the angle between the rotationally oriented adjacent links allows for smoother, substantially continuous rotation of the tubular body of the tool.

In some embodiments, an outer diameter of the tubular body 152 ranges between, for example, 2-10 mm, 4-6.5 mm, 5-20 mm, or intermediate, larger or smaller diameters. Optionally, the tool 150 is configured to form a bore or to ream an existing bore in a bone of similar diameters.

FIG. 3B shows tool 150 in a straight configuration. In some embodiments, the tool 150 comprises a cutting head 154 located at a distal end of the tubular body 152.

Figure 4:
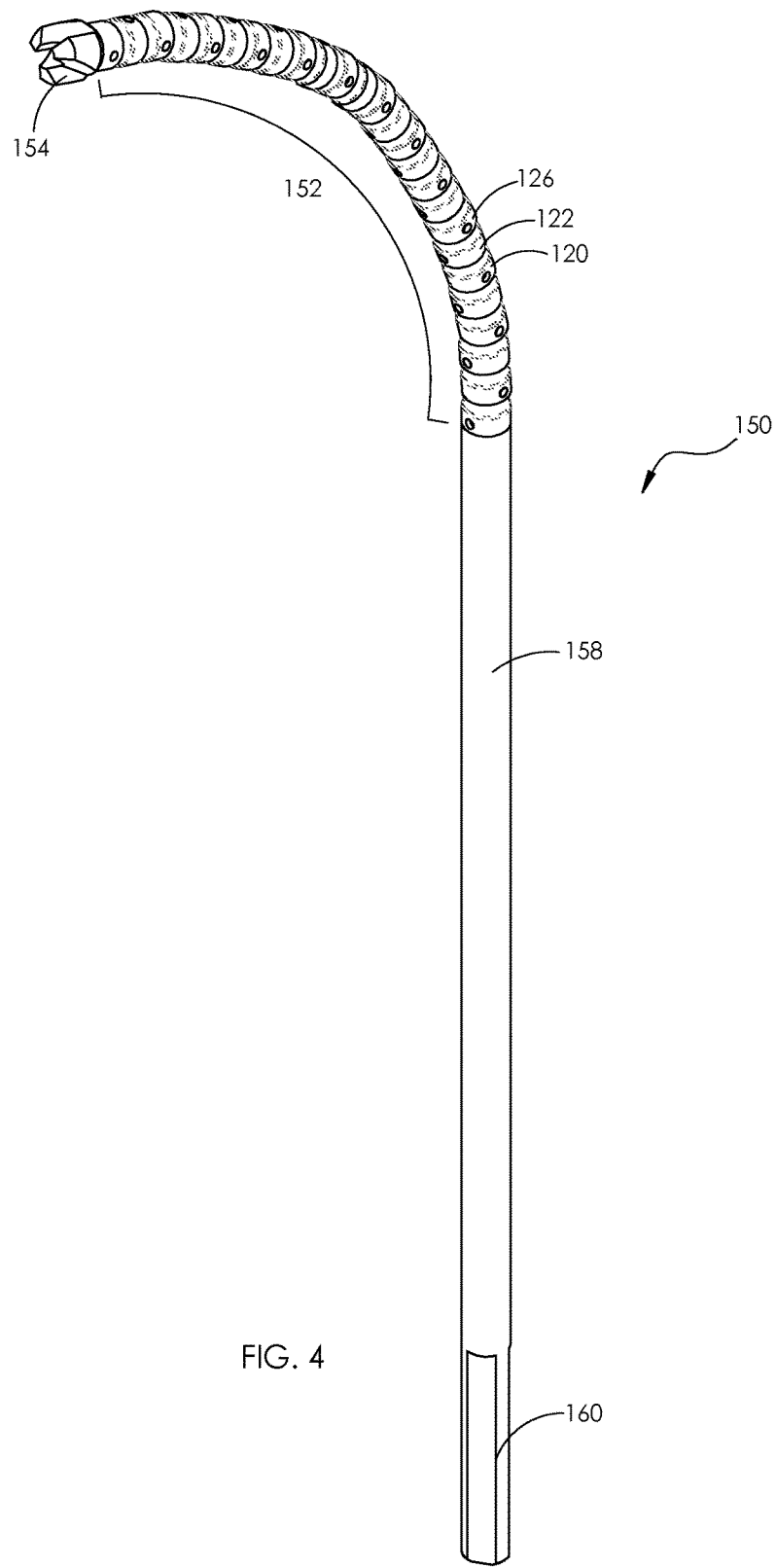
FIG. 4 is a side-view simplified illustration of a flexible bone tool bent into an L-curve, according to some embodiments of the invention.

Reference is now made to FIG. 4, which is a perspective view simplified illustration of the flexible bone tool 150 bent into an L-shaped curve, according to some embodiments of the invention.

In some embodiments, the tubular body 152 of the flexible bone tool 150 is configured to bend into a bending radius R, e.g., 30 mm, 40 mm, 60 mm or intermediate, larger or smaller radii. Optionally, the tubular body 152 is configured to bend into an L-shaped curve, for example such that the rotational axis of distal cutting head 154 is at an angle between 0 and 180 degrees in respect to the rotational axis of handle 158. In some embodiments, the angle is 90 degrees. A configuration in which the flexible bone is flexed into an L-shaped or even a U-shape curve may be advantageous in procedures that require accessing the bone through a curved path, for example by going around anatomical structures, for example during spine surgery. In some embodiments, rotating the tool around its axis when the tool is flexed into the U-shaped curve provides for drilling and/or widening a bore in the bone while torque is applied from a substantially opposite direction, e.g., from a proximal portion of the tool 150, and is transferred by the articulated links to the distal cutting head 154.

Figure 6A:
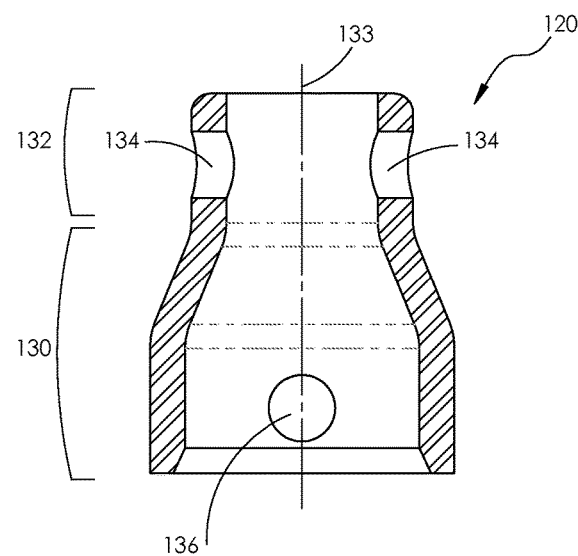
FIGS. 6A and 6B are sectional view simplified illustrations of the single link of FIG. 5, section being taken along lines A-A in FIG. 5 in accordance with some embodiments of the invention.
Figure 5:
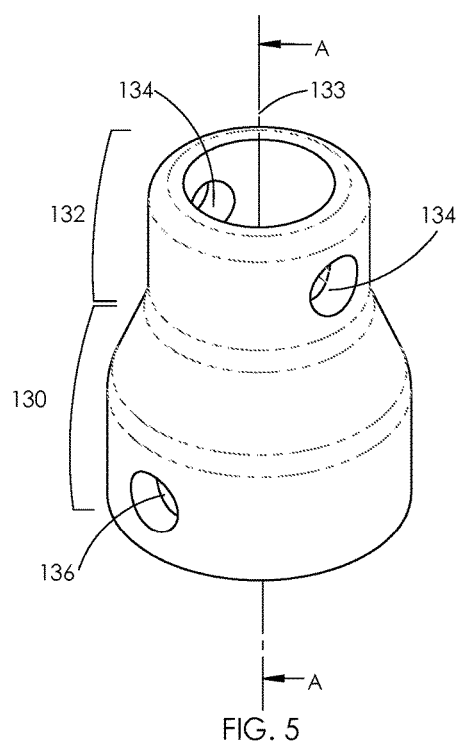
FIG. 5 illustrates a perspective and cross-section view simplified illustration of a single link, according to some embodiments of the invention.
Figure 6B:
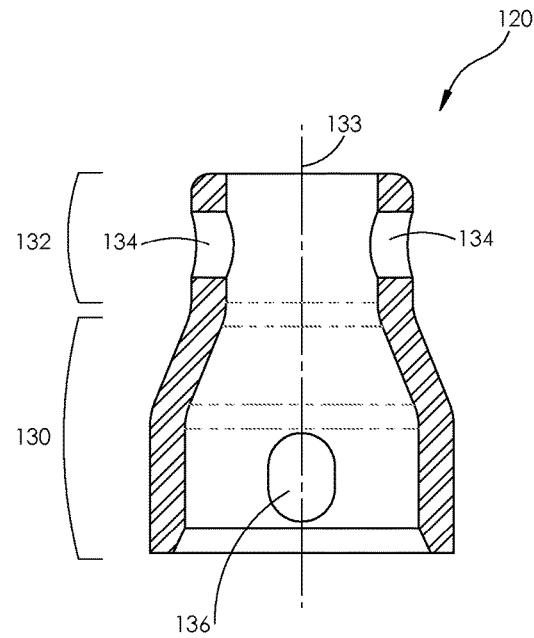

Reference is now made to FIG. 5, which is a pictorial view simplified illustration of a single link 120 according to some embodiments of the invention. Reference is additionally made to FIGS. 6A and 6B, which are sectional view simplified illustrations of embodiments of the single link 120 of FIG. 5, taken along lines A-A.

In some embodiments, a single link 120, 122 and/or 126 is made of stainless steel and is manufactured by means of deep drawing.

As described in detail elsewhere herein, a single link 120, 122 and/or 126 comprises a proximal receiving portion 130, and a distal engaging portion 132. An engaging portion 132 is sized and fitted to be received within a receiving portion 130 of a subsequent distal link.

In some embodiments, engaging portion 132 is generally cylindrical and has at least two diametrically opposed apertures 134, a diameter spanning between apertures 134 being transversely oriented with respect to longitudinal axis 133. Alternatively and optionally, engaging portion 132 defines a different outer profile, such as hexagonal, oval, and/or other outer profile configured to be received within the receiving portion 130 of the subsequent link.

In some embodiments, receiving portion 130 comprises a generally cylindrical first proximal segment and an inwardly tapering second distal segment and two diametrically opposed apertures 136 located in a wall of the first proximal segment of the receiving portion and extending along an axis which is transversely oriented with respect to longitudinal axis 133. Alternatively and optionally, receiving portion 130 defines a different outer profile, such as hexagonal, oval, and/or other outer profile configured to be received within the corresponding engaging portion 132 of the subsequent link.

Apertures 134 are positioned on a plane which is generally perpendicular to the plane on which apertures 136 are positioned.

In some embodiments, the outer profile of engaging portion 132 of link 120 is of a generally smaller outer diameter than an inner diameter of a receiving portion 130 of subsequent link 122, so as to fit within the receiving portion 130.

In some embodiments, the inner profile of receiving portion 130 is of a generally larger inner diameter than an outer diameter of the engaging portion 132 of the proximal link 120, so as to receive the engaging portion 132 therein.

In some embodiments, apertures 136 are positioned at an angle of typically 90 degrees with respect to apertures 134.

In some embodiments, each link comprises a plurality of apertures 134 and 136 and corresponding connecting pins 128 and/or 124, for example 2, 3, 4, 5, 6, 10 extensions/pins or intermediate, larger or smaller number. Optionally, links of a single tool comprise different numbers of extensions/pins. Optionally, the number of extensions/pins determines the extent of movement of the links relative to each other. For example, a single aperture may provide for a higher degree of freedom of movement relative to a larger number of apertures, for example movement in the axial and/or radial directions.

In some embodiments, the diameter of a single link, such as 120, 122 and 126 is within the range of 2-6.5 mm and the length of a single link such as 120, 122 and 126 is within the range of 4-8 mm.

In the exemplary embodiments shown in FIGS. 6A and 6B, aperture 136 may be circular (FIG. 6A) or oblong (FIG. 6B). In some embodiments, either one or both apertures 136 and/or 134 can be oblong. The oblong aperture 136/134 provides limited movement of a first link 120 axially along an axis of rotation of said tool relative to a preceding or following consecutive link 120.

Figure 7:
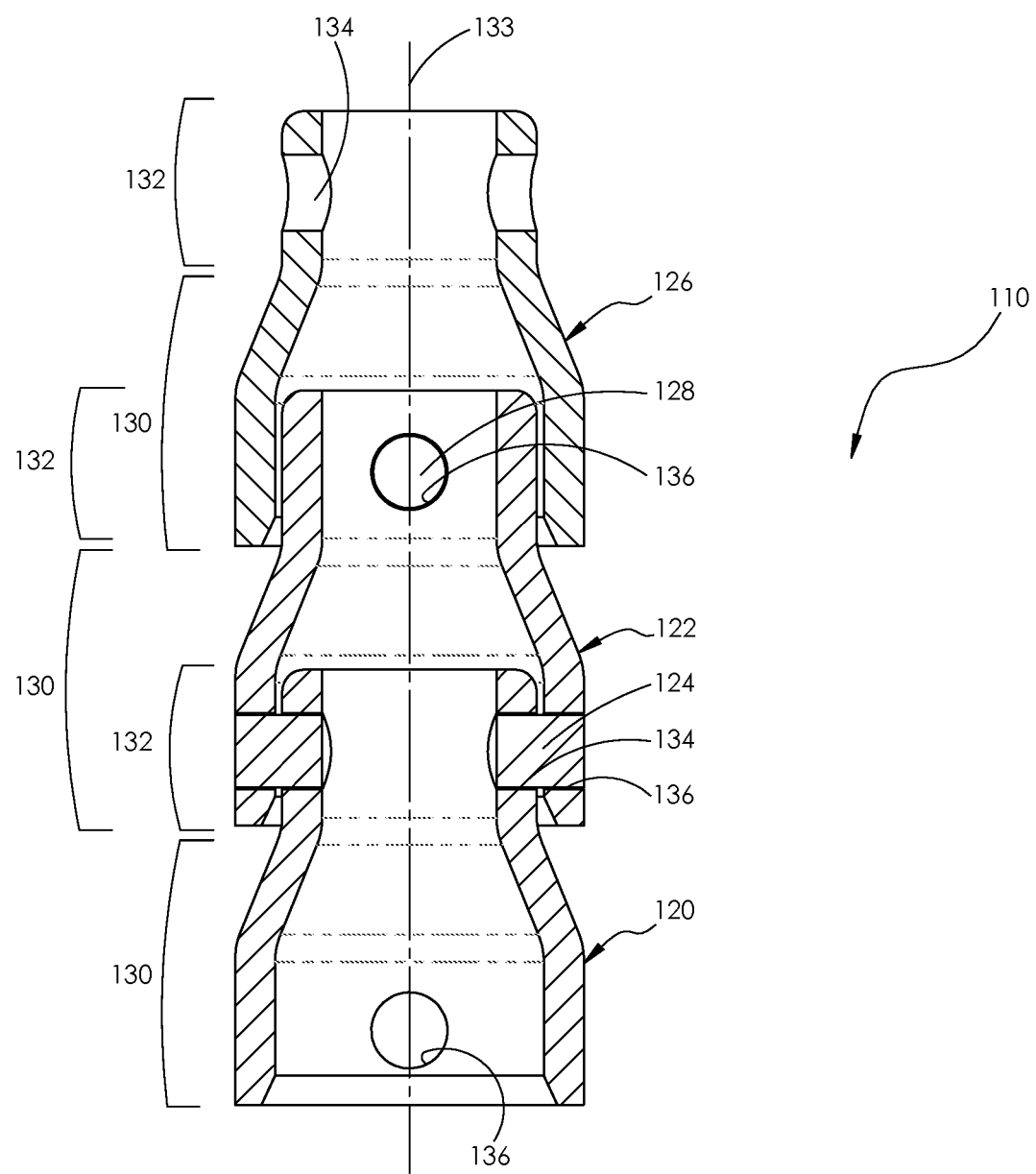
FIG. 7 is a sectional view simplified illustration of the link of FIG. 5, a receiving subsequent link, rotationally oriented relative to the link of FIG. 5, and the links coupled to each other according to some embodiments of the invention, section being taken along lines A-A in FIG. 3B.

Reference is now made to FIG. 7, which is a sectional view simplified illustration of arrangement of the links of flexible bone tool 150 in accordance with some embodiments of the invention.

As shown in the exemplary embodiment of FIG. 7, links 120, 122 and 126 are axially aligned, each link coupled to and axially rotated (e.g., rotated about its longitudinal axis) in respect to a subsequent contiguous distal or preceding contiguous proximal link. In some embodiments, the links are coupled to and rotated at an angle of 90 degrees with respect to each other such that apertures 136 of one are aligned with apertures 134 of a preceding contiguous proximal link. In some embodiments, a circumferential contact area between the links increases when the distal cutting head 154 of the tool 150 contacts the bone, and the links are axially approximated towards each other. An increased circumferential contact area may provide an advantage during drilling, for example, since the increased contact area contributes to dispersing the load and thereby reducing the load acting on the tooth-like extensions/pins that hold the links together.

In the embodiment depicted in FIG. 7, the link 120 and a subsequent, receiving link 122 are oriented rotationally perpendicular relative to each other. The apertures 136 of link 120, at a cross section, are shown to extend on a plane which is perpendicular to the plane of the cross section of apertures 136 of link 122.

In some embodiments, links 120, 122 and 126 are engaged with each other using connecting pins 124 and 128, as described in detail elsewhere herein. In the example of FIG. 7, apertures 136 of link 122 are aligned with and abut apertures 134 of link 120 and the connecting pins 124 driven through both apertures 124 and 136 secure the two links together, while providing a rotational degree of freedom, as described in greater detail elsewhere herein.

In some embodiments, one or more dimensions of a link are selected to provide for a certain bending radii range of a tubular body comprising a plurality of links. Optionally, the extent of the bending radius is determined by link dimensions e.g., dimensions of contact areas between every two subsequent links, a length of the engaging portion 132 of link 120; an outer diameter of the engaging portion 132 of link 120 and the inner diameter of the receiving portion 130 of the receiving link 122. In some embodiments, a more flexible tubular body which is configured to bend into smaller bending radii can be provided by one or more of: increasing the length dimension; decreasing the outer diameter dimension and increasing the inner diameter dimension. Optionally, selecting the link dimensions for example as described would result in a larger space remaining unoccupied between two subsequent links, so that during bending the links will be more free to rotate and allow a higher degree of flexion of the tubular body 152.

Figure 8A:
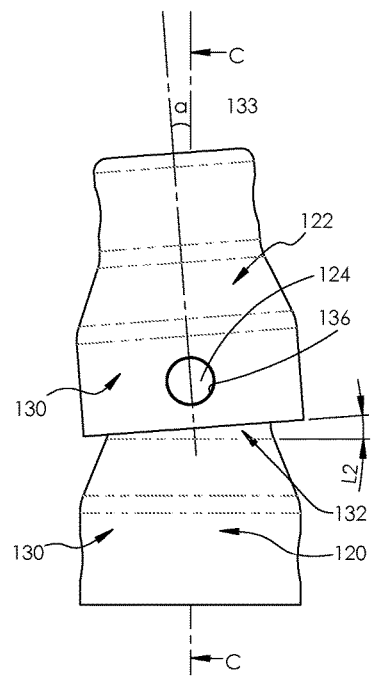
FIGS. 8A and 8B illustrate a partial perspective view simplified illustration of the coupled links according to some embodiments of the invention.
Figure 8C:
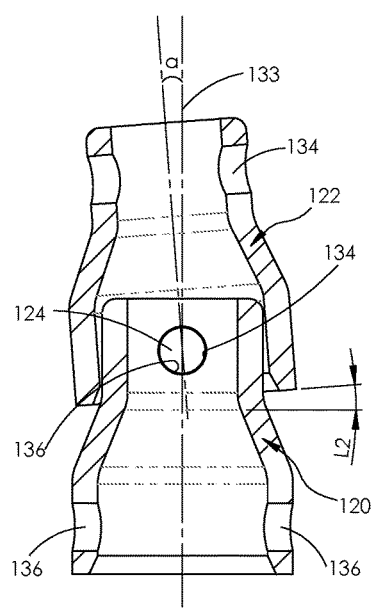
FIG. 8C is a sectional view simplified illustration of FIG. 8A, section being taken along lines C-C in FIG. 8A.
Figure 8B:
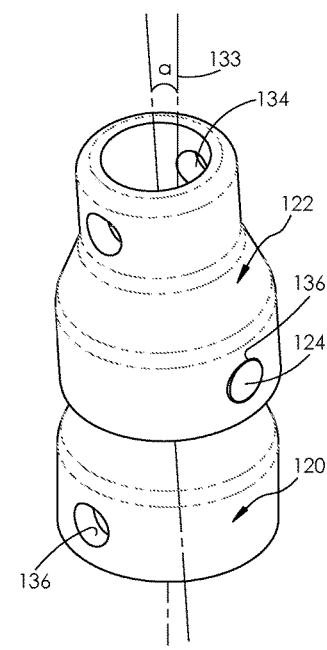

Reference is now made to FIGS. 8A and 8B, which illustrate a partial pictorial view and 8C, which illustrate a partial sectional simplified illustration of arrangement of the coupled links of flexible bone tool 150 in accordance with some embodiments of the invention. As shown in FIGS. 8A, 8B and 8C a distal link 122, is shown coupled to a received preceding proximal link 120. Additionally and optionally distal link 122 is coupled to and rotated relative to proximal link 120 e.g., 90 degrees or one quarter turn. The links are shown in a bent orientation. Reference is additionally made to FIG. 8C, which illustrates a sectional view illustration of FIG. 8A, section being taken along lines C-C in FIG. 8A.

Optionally, an axial gap extending over a distance L2 exists between at least a portion of the circumferences of the adjoined links 120 and 122 Optionally, the extent of L2 is affected by one or more of: the number of apertures 134 and 136 and corresponding connecting pins 124 coupling the links together. In some embodiments, consecutive links 120 are coupled by one or more pins 124/128 such that once coupled, an engaging portion 132 is positioned within receiving portion 130. Pins 124A and 124B coupling engaging portion 132 within receiving portion 130 stop engaging portion 132 from being fully inserted into receiving portion 130 leaving a volume (e.g., gap) within receiving portion 130 of the receiving link that remains unoccupied by the engaging portion 132, enabling movement (e.g., pivotal movement) of the engaging portion 132 inside the receiving lumen; the bending radius of the tubular body 152 or a segment thereof and tension force acting on the tubular body 152.

In some embodiments, the tool 150 is advanced along a curved path inside the bone. Optionally, the tool follows a path defined by guide wire 156 as long as the bending radius of the tubular body is compatible with the bending radius of the guide wire. Additionally or alternatively, the tool 150 is advanced along a straight path.

In some embodiments, the tubular body is advanced a certain depth into the bone relative to the surface of the bone, for example a depth ranging between 1 mm to 5 cm. Optionally, the tubular body is advanced to cross through the bone, for example such that cutting head 154 exits a face of the bone which opposes the face through which the tool was inserted.

In some embodiments, the tool is rotated around its axis to advance it into the bone. Optionally, rotary motion is applied by coupling a drill to the head of the proximal holding portion 160. In some embodiments, torque applied onto a proximal end of the tool is transferred by the connected links to a distal end of the tool 150. In some embodiments, the tool is configured to transfer torque within the range of, for example, 3 N*cm to 5 N*cm, such as 3.2, 4.5, 4.8 N*cm or intermediate, higher or lower values.

In some embodiments, for example when the flexible bone tool is used for drilling a bore in the bone, the tubular body may comprise a flexible core, for example made of Nitinol, stainless steel. Optionally, the core is selected to be flexible enough to allow bending of the tubular body, yet rigid enough to support the links during drilling when the tubular body needs to withstand relatively strong forces from the bone tissue in order to penetrate the bone.

It is particularly seen in FIGS. 8A-8C that in a bent orientation of the tool 150, the links 120 and 122 are positioned at an angle "a" with respect to each other, thus the proximal end of receiving portion 130 of link 122 is angularly displaced with respect to its orientation at rest, as shown in FIG. 7. In some embodiments, angle "a" may be in the range of 2-10 degrees. In some embodiments, the angle of rotation "a" between two subsequent link may be in the range of 5-8 degrees.

Figure 9:
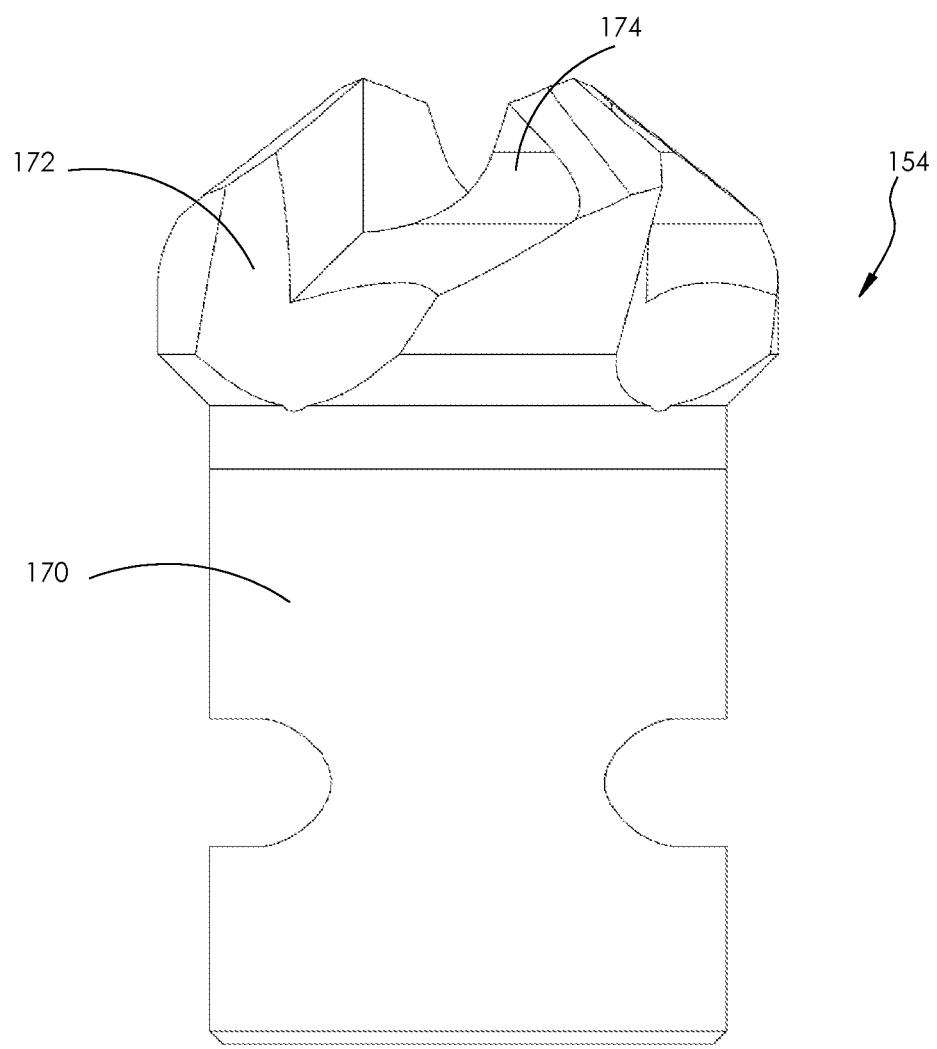
FIG. 9 illustrates a side-view simplified illustration of a cutting head according to some embodiments of the invention.

Reference is now made to FIG. 9, which is a side view simplified illustration of a bone tissue removal link according to some embodiments of the invention. In the example shown in FIG. 9 distal bone tissue removal link comprises a cutting head 154. In some embodiments, distal bone tissue removal link comprises a bone reamer. In some embodiments, cutting head 154 is configured to engage the flexible bone tool 150.

In some embodiments, cutting head 154 comprises a proximal receiving portion 170 structured to receive an engaging portion of a preceding link. Optionally, receiving portion 170 includes an internal recess for example as described elsewhere herein. In some embodiments, cutting head 154 includes a distal cutting portion 172, comprising one or more cutting edges 174 for penetrating the bone and/or for enlarging an existing bore in the bone.

In some embodiments, a cross sectional area of cutting portion 172 is larger than a cross sectional area of receiving portion 170 (and optionally of the rest of the tubular body of the tool). In an example, a maximal diameter of cutting portion 172 is at least 5%, 10%, 20%, 40% or intermediate, larger or smaller percentages larger than a diameter of receiving portion 170.

In some embodiments, a proximal portion of the tool is adjustable. Optionally, a structure of the proximal head is selected to engage a surgical tool, such as a drill, reamer, screw driver, and/or other tools. Optionally, the proximal head is adapted to connect to a tool suitable for applying rotary motion to the flexible bone tool. For example, the proximal head may have a hexagonal profile, a squared profile, a round profile, and/or any other profile shaped and sized to be engaged by the tool. In some embodiments, dimensions of the proximal portion (such as an axial length and/or diameter) are selected according to the need.

In some embodiments, a kit is provided. Optionally, the kit comprises a plurality of separate links; a plurality of cutting heads having different structures and/or sizes; a flexible bone tool comprising a proximal holding portion and a tubular body of an initial base length (for example a length ranging between 30-120 mm, such as 40 mm, 60 mm, 100 mm or intermediate, longer or shorter tubular body).

Additionally or alternatively and optionally, attachment and/or detachment of links is performed manually, for example by a user employing a dedicated tool as explained elsewhere herein.

It is a particular feature of an embodiment of the present invention that the tubular tool 152 may be used as a disposable tool, since the tool is manufactured using deep drawing and connection of pins, providing for inexpensive manufacturing process.

Figure 10:
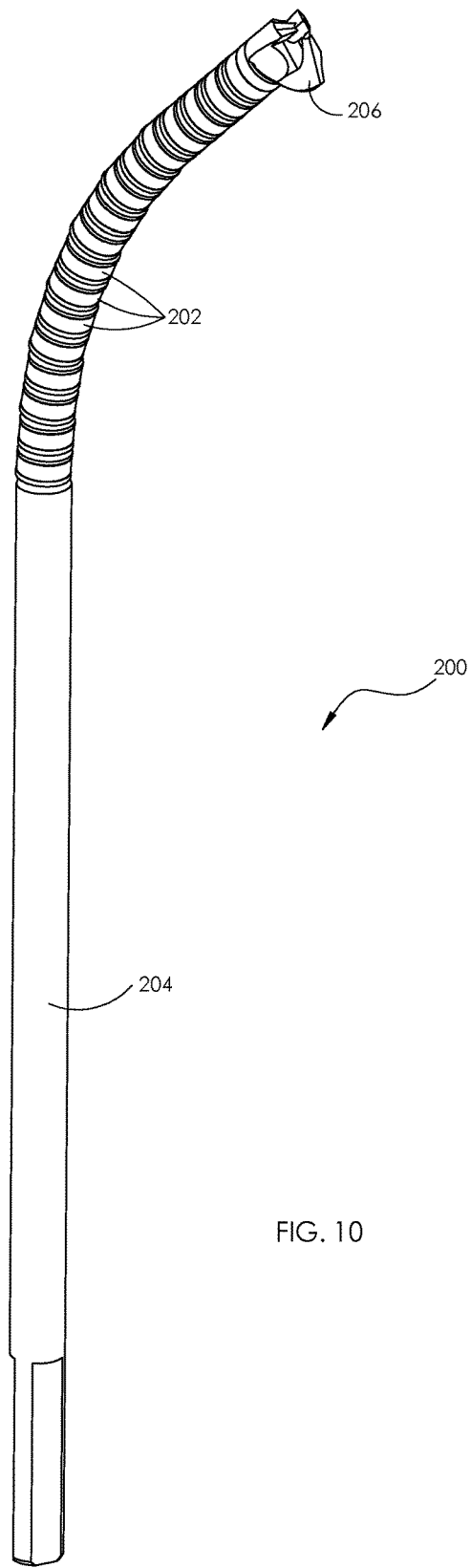
FIG. 10 is a simplified pictorial illustration of an embodiment of an assembled flexible bone tool, constructed and operative in accordance with some embodiments of the present invention.
Figure 11:
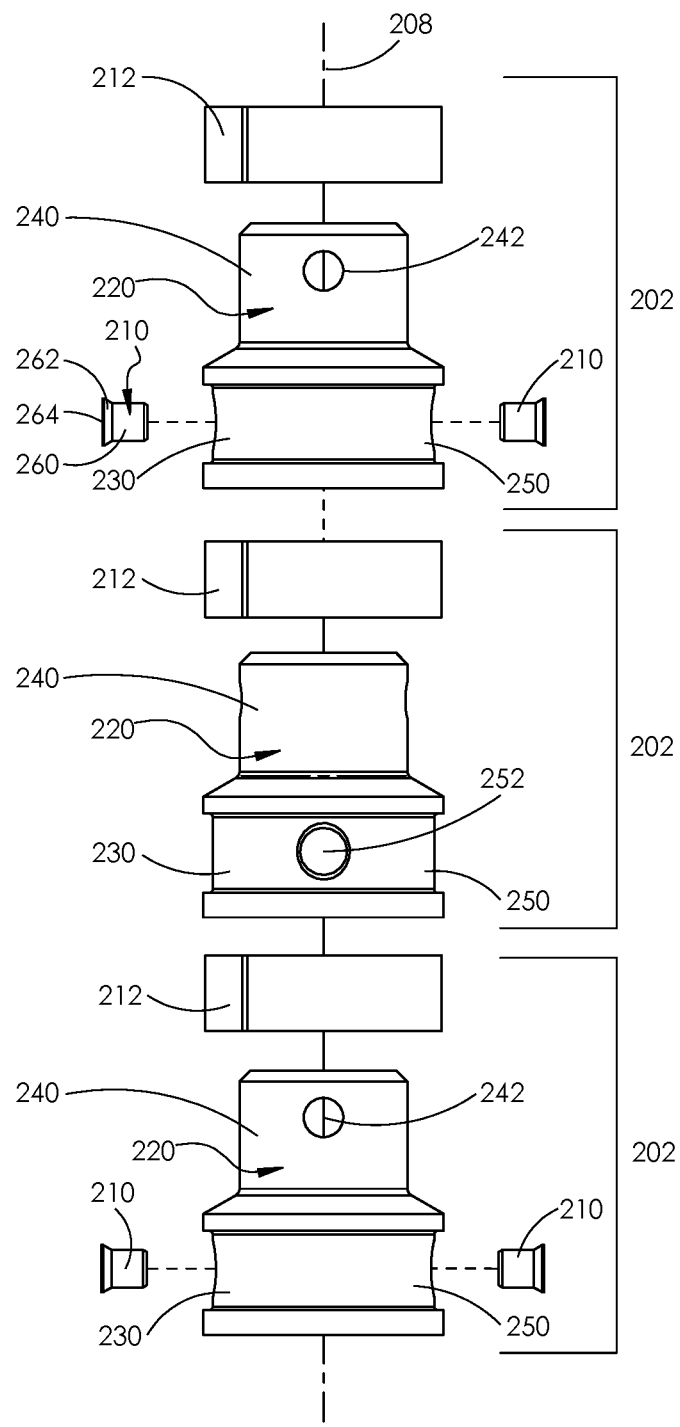
FIG. 11 is a simplified partial exploded view simplified illustration of link structure of an embodiment of the flexible bone tool of FIG. 10.

Reference is now made to FIG. 10, which is a simplified pictorial illustration of an assembled flexible bone tool, constructed and operative in accordance with some embodiments of the present invention and to FIG. 11, which is a simplified partial exploded illustration of link structure of the flexible bone tool of FIG. 10.

An embodiment of a flexible bone tool 200 comprising a plurality of interconnected link assemblies 202 is seen in FIG. 10. The flexible bone tool 200 includes a shaft or proximal holding portion 204 at its proximal end, a plurality of interconnected link assemblies 202, adapted to be pivotably displaced relative to each other and a cutting head 206 at its distal end.

In some embodiments, the link assemblies 202 are arranged along a common longitudinal axis 208 at rest. In some embodiments, the interconnected link assemblies define a substantially tubular, bendable body. In some embodiments, the bone tool comprises a cutting head configured at a distal end of the tubular body. Optionally, the cutting head is shaped and/or sized to cut a bore in the bone, allowing the tool to function as a drill bit. Additionally or alternatively and optionally, the cutting head is shaped and/or sized to widen an existing bore in the bone, for example when rotary motion is applied to the tool, for example to a proximal holding portion of the tool, allowing the tool to function as a reamer. In some embodiments, the bone tool comprises a holding portion configured proximally to the tubular body. In some embodiments, the proximal holding portion may be engaged by a user, e.g., a physician, and/or by an additional tool, e.g., a drill. In some embodiments, the tubular body and optionally the proximal holding portion are cannulated. Optionally, the cannulated tool is delivered over a guide wire, guide pin, suture and/or other elongated elements that can fit within and/or be passed through the cannulation.

In some embodiments, a guide wire is introduced to the targeted bone. Optionally, an initial bore is drilled in the bone, for example by advancing the guide wire into the bone, e.g., with the aid of a drill. In some embodiments, at least a portion of the guide wire is bent into an arch or other curved profile. Optionally, the guide wire is bent into a selected curvature after at least a part of the wire (e.g. a distal end) has been anchored to the targeted bone.

In some embodiments, each of the link assemblies 202 is configured to be connected to a subsequent, more distal link assembly 202 by means of two connecting pins 210 and a fixator 212. Each link assembly 202 comprises a link 220, having a receiving portion 230 and an engaging portion 240. In some embodiments, links 220 of link assembly 202 are configured such that an engaging portion 240 is received within a receiving portion 230 of a subsequent link 220.

In some embodiments, engaging portion 240 is generally cylindrical and has two diametrically opposed apertures 242. Alternatively, engaging portion 240 defines a different outer profile, such as hexagonal, oval, and/or other outer profile configured to be received within a receiving portion 230 of the subsequent link having corresponding geometry.

In some embodiments, receiving portion 230 has a generally cylindrical outer profile with a circumferential annular recess 250 and two diametrically opposed apertures 252 formed therewithin. Alternatively and optionally, engaging portion 240 defines a different outer profile, such as hexagonal, oval, and/or other outer profile configured to be received within the corresponding receiving portion 230 of the subsequent link having corresponding geometry.

In some embodiments, the outer diameter of engaging portion 240 of one link 220 is of a generally smaller outer diameter than an inner diameter of the receiving portion 230 of subsequent link 220, so as to fit within the receiving portion 230.

In some embodiments, the inner diameter of receiving portion 230 is generally larger than an outer diameter of the engaging portion 240 of the proximal link 220, so as to receive the engaging portion 240 therein.

In some embodiments, apertures 242 are positioned at an angle of typically 90 degrees with respect to apertures 252.

In some embodiments, each subsequent link 220 is positioned at an angle of typically 90 degrees with respect to another link 220, such that apertures 242 of a first link 220 are adapted to be aligned with apertures 252 of the second link 220.

It is noted that connecting pins 210 include a generally cylindrical portion 260 and a generally outwardly tapered portion 262, defining an outwardly facing surface 264.

In some embodiments, each link comprises a plurality of apertures 242 and 252 and connecting pins 210, for example 2, 3, 4, 5, 6, 10 or intermediate, larger or smaller number of extensions/pins. Optionally, links of a single tool comprise different numbers of extensions/pins. Optionally, the number of extensions/pins determines the extent of movement of the links relative to each other. For example, a single aperture may provide for a higher degree of freedom of movement relative to a larger number of apertures, for example movement in the axial and/or radial directions.

In some embodiments, the links are formed of metal, such as stainless steel. Additionally or alternatively, the links are formed of a biocompatible plastic, such as polycarbonate and/or isoplast.

In some embodiments, at least one link and/or at least the tubular body and/or cutting head are disposable.

In some embodiments, the magnitude of torque transferred by the links is sufficient for drilling into the bone tissue, for example ranging between 3 N*cm-15 N*cm. Optionally, the tubular body is configured to transfer a magnitude of torque ranging between 1 N*cm to 150 N*cm, such as 5-20 N*cm, 10-40 N*cm, 50-100 N*cm. In some embodiments, the matching non-circular geometries of the engaging portion and the inner lumen of the receiving portion are selected to allow axial rotation of the link assemblies 202 relative to each other only to an extent in which sufficient torque can still be transferred between the links.

Figure 12A:
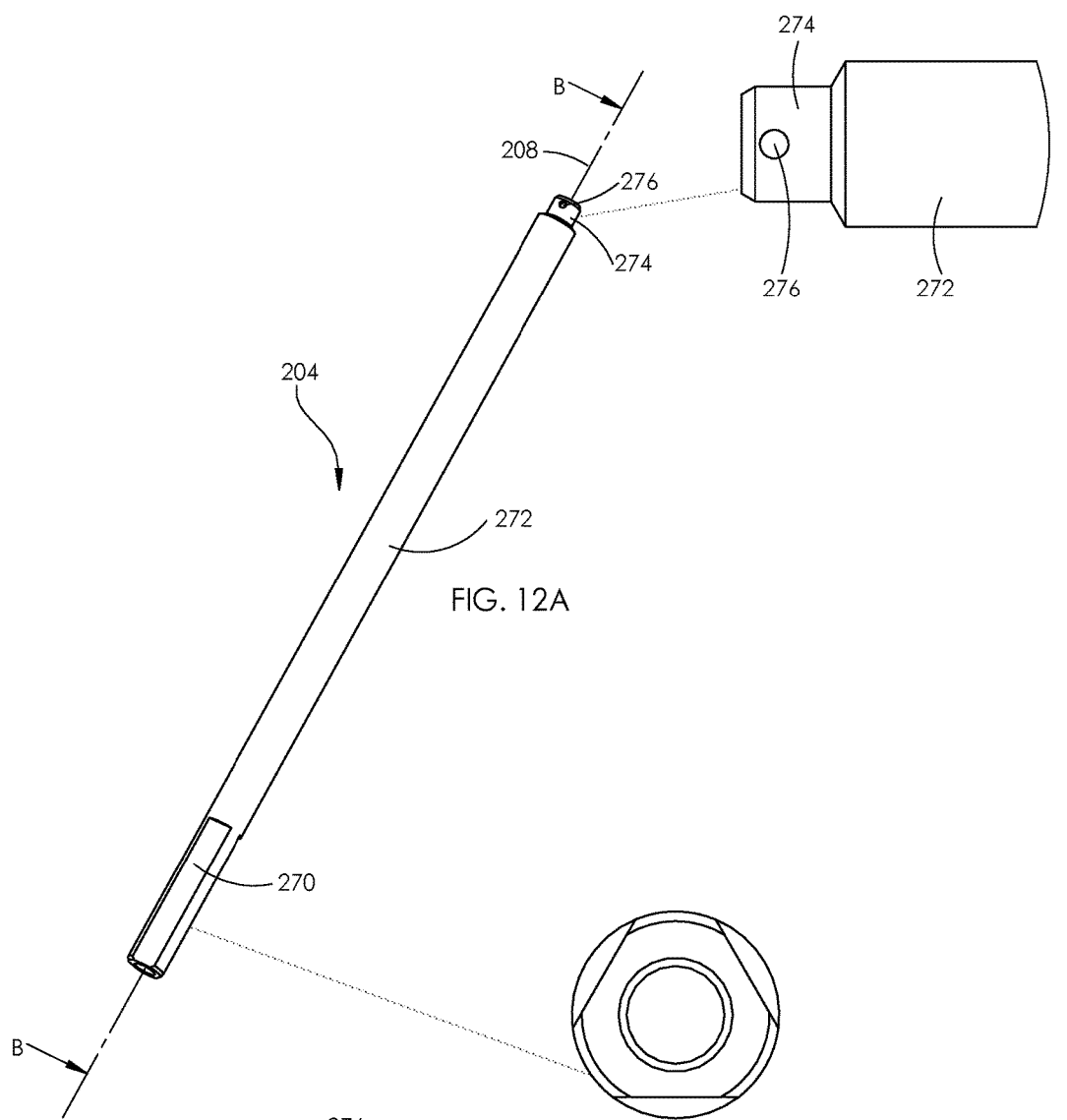
FIGS. 12A and 12B are perspective view and sectional views simplified illustrations of a shaft in accordance with an embodiment of the flexible bone tool of FIG. 10, section being taken along lines B-B.
Figure 12B:
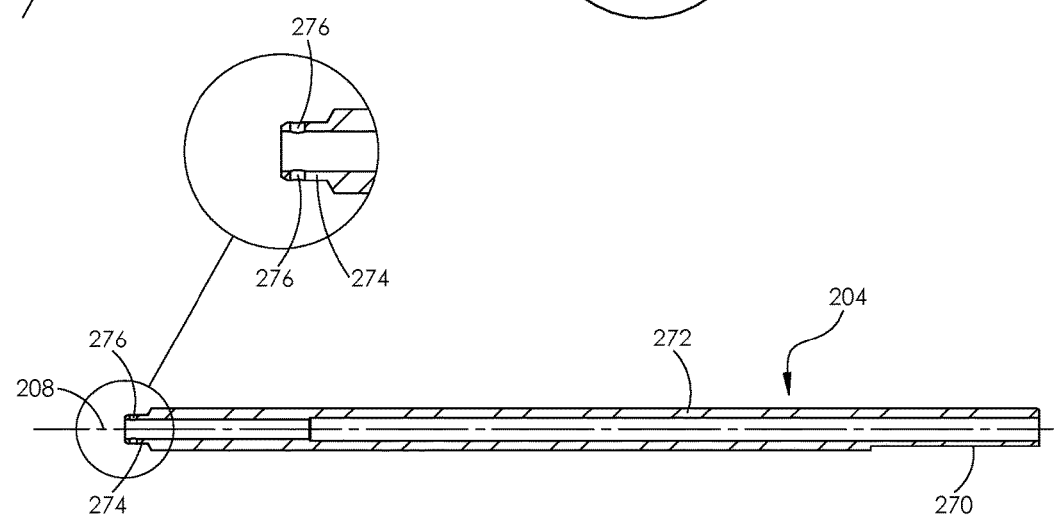

Reference is now made to FIGS. 12A & 12B, which are perspective view and sectional view simplified illustrations of the shaft 204, of the flexible bone tool 200, section being taken along lines B-B in accordance with some embodiments of the invention.

In some embodiments, shaft or proximal holding portion 204 is cannulated. In some embodiments, cannulated shaft 204 comprises a proximal gripping end 270, an intermediate generally cylindrical portion 272 and a proximal connection portion 274. As shown in the embodiment depicted in FIGS. 12A and 12B, two diametrically opposed apertures 276 are formed in proximal connection portion 274 for attachment to the most proximal link assembly 202 by means of connection pins 210.

Figure 13A:
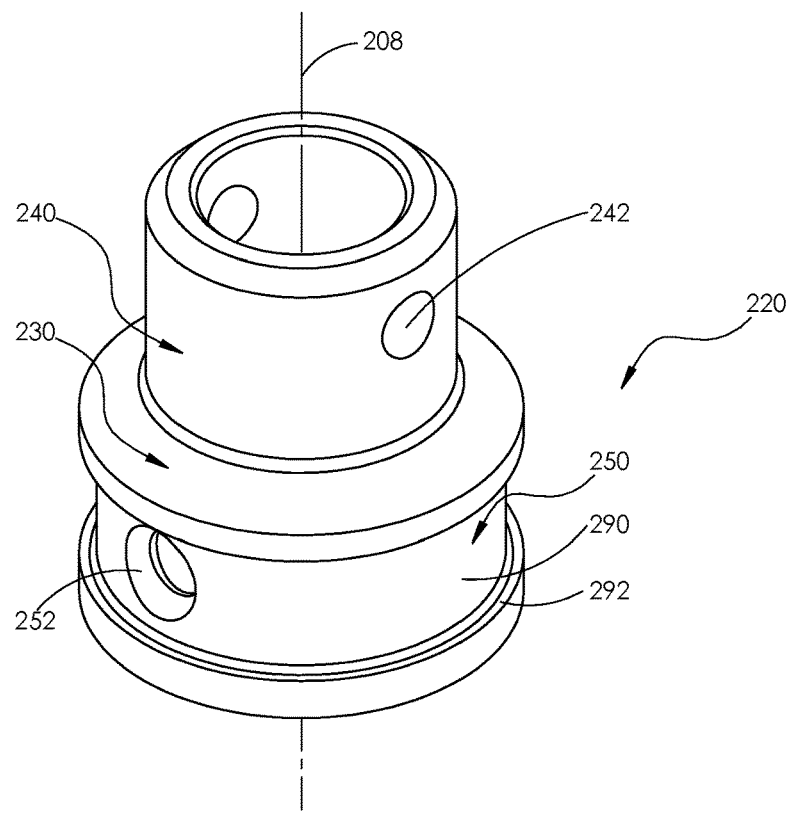
FIGS. 13A and 13B are perspective view and sectional view simplified illustrations of an embodiment of a single link of the flexible bone tool of FIG. 10.
Figure 13B:
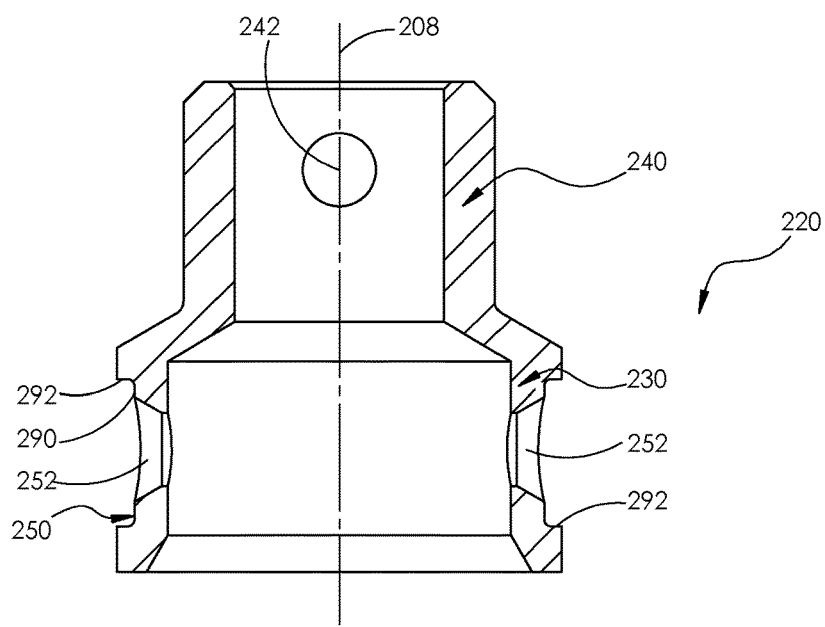

Reference is now made to FIGS. 13A & 13B, which are perspective view and sectional view simplified illustrations of a single link 220 of the flexible bone tool 200. In some embodiments, link 220 is made of e.g., stainless steel and is manufactured by means of deep drawing.

As described in detail above, in some embodiments, link 220 an engaging portion 240, sized and fitted to be received within a receiving portion 230 of the subsequent link 220.

In some embodiments, engaging portion 240 is generally cylindrical and has two diametrically opposed apertures 242 extending along an axis which is transversely disposed with respect to longitudinal axis 208. Alternatively, engaging portion 240 defines a different outer profile, such as hexagonal, oval, and/or other outer profile configured to be received within the receiving portion 230 of the subsequent link.

In some embodiments, receiving portion 230 is of a generally cylindrical outer profile, having circumferential annular recess 250 formed on an outer surface thereon and two diametrically opposed apertures 252 formed within recess 250 and extending along an axis which is transversely oriented with respect to longitudinal axis 208. Alternatively, receiving portion 230 defines a different outer profile, such as hexagonal, oval, and/or other outer profile configured to be received within the corresponding engaging portion 240 of the subsequent link.

Apertures 252 are positioned on a plane which is generally perpendicular to the plane on which apertures 242 are positioned.

Recess 250 defines an outwardly facing surface 290 and two shoulder edge surfaces 292 confining the recess 250.

In some embodiments, the outer profile of engaging portion 240 of a first link 220 is of a generally smaller outer diameter than an inner diameter of a receiving portion 230 of subsequent link 220, so as to fit within the receiving portion 230.

In some embodiments, the inner diameter of receiving portion 230 is generally larger than an outer diameter of the engaging portion 240 of the proximal link 220, so as to receive the engaging portion 240 therein.

In some embodiments, apertures 252 are positioned at an angle of typically 90 degrees with respect to apertures 242.

Figure 14A:
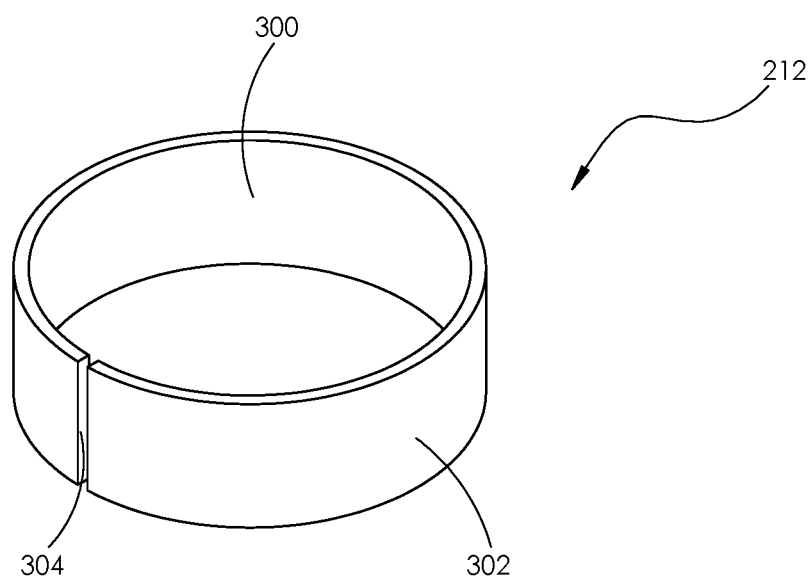
FIGS. 14A, 14B and 14C are perspective view simplified illustrations of exemplary embodiments of link assembly fixation elements.
Figure 14B:
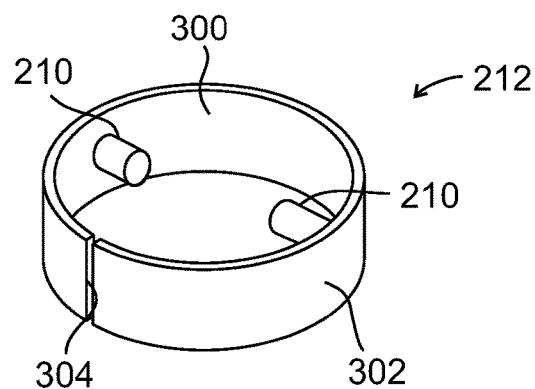
Figure 14C:
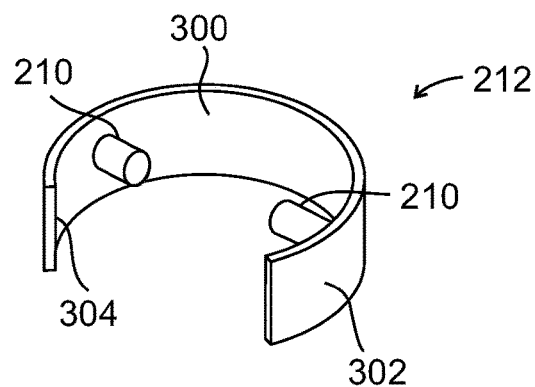

In some embodiments, the diameter of the single link 220 is within the range of 2-6.5 mm and the length of the single link 220 is within the range of 4-8 mm. Reference is now made to FIGS. 14A, 14B and 14C which are perspective view simplified illustrations of exemplary embodiments of link assembly fixation elements.

As shown in FIG. 14A, a fixation element 212 is an integrally made annular element of generally annular shape, made of resilient or semi-resilient material e.g., stainless steel, or any other biocompatible material. Fixation element 212 defines an inwardly facing surface 300, an outwardly facing surface 302 and a slit 304, which enables the fixation element 212 to deform resiliently upon application of stress. In some embodiments, when applied, the fixator 212 envelopes at least a portion of the link 220 at the level of apertures 252 and blocks pins 210 from radially exiting apertures 252.

In some embodiments and as shown in FIGS. 14B and 14C, fixation element 212 includes at least one pin 210 rigidly coupled to inwardly facing surface 300. In the examples of FIGS. 14B and 14C each fixation element comprises a pair of diametrically opposed pins 210. In some embodiments, e.g., FIG. 14B, fixation element 212 is similar in shape to fixation element 212 of FIG. 14A. In some embodiments, fixation element 212 has semi-circle geometry as shown in e.g., FIG. 14C. In some embodiments, fixation elements 212 comprising one or more pins 210 support pivoting movement of consecutive links coupled by pins 210 such as, for example pins 210 shown in FIGS. 14B and 14C in respect to each other. In some embodiments, each of fixation elements 212 shown in FIGS. 14A-14C comprises a snap-fit attachment to a corresponding link 220.

Figure 15:
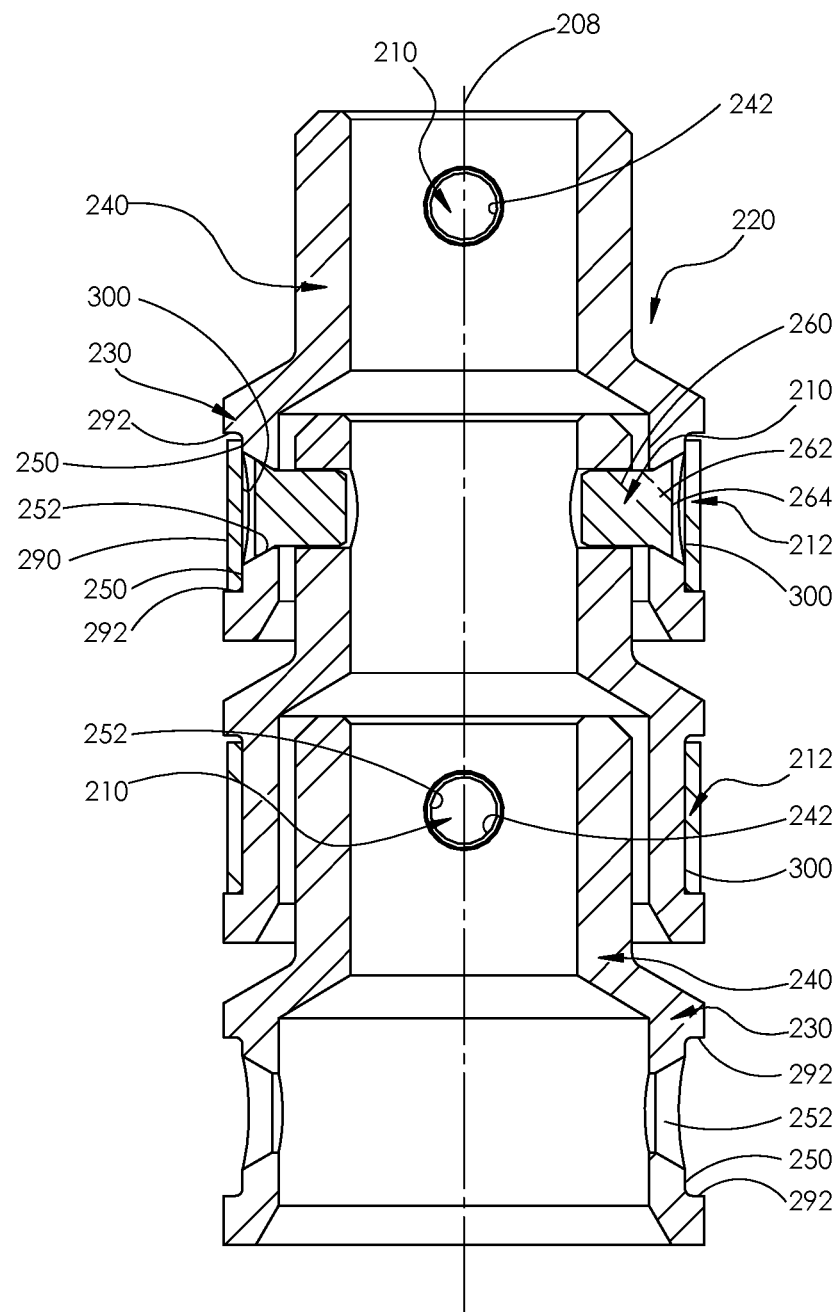
FIG. 15 is a partial sectional view simplified illustration taken along several subsequent link assemblies of an embodiment of the flexible bone tool of FIG. 10.

Reference is now made to FIG. 15, which is a partial sectional view simplified illustration taken along several subsequent link assemblies of the flexible bone tool 200. In the embodiment depicted in FIG. 15, link assemblies 202 are coupled to each other, in a resting, unstressed orientation.

In the embodiment shown in FIG. 15, it can be seen that a proximal link 220 and a subsequent distal receiving link 220 are perpendicularly oriented relative to each other. The apertures 252 of the proximal link 220, at a cross section, are shown to extend on a plane which is perpendicular to the plane of the cross section of apertures 242 of distal link 220. The links 220 are coupled to each other using connecting pins 210. Apertures 242 of a proximal link 220 are aligned with apertures 252 of a distal link 220 and the connecting pins 210 are inserted through both apertures 242 and 252 and secure the two links together, while providing rotational degree of freedom, as seen further in FIGS. 16A-16C.

It is a particular feature of an embodiment of the present invention that the connecting pins 210 cannot be fully inserted into the interior of a link 220, due to the fact that the connecting pins 210 have outwardly tapered portion 262. It is a further particular feature of an embodiment of the present invention that fixation element 212 is mounted within recess 250 of each link 220 and is confined by shoulder edges 292 of link 220. The inwardly facing surface 300 of fixation element 212 engages outwardly facing surface 264 of connecting pins, thus preventing the connecting pins 210 from falling out of apertures 242 and 252, and thus the connecting pins 210 are securely held within the links 220 and securely retain the plurality of links 220 together. It is noted that it is possible mounting the fixation element 212 onto the link 220 due to its spring characteristics provided by slit 304 formed therein.

Figure 16:
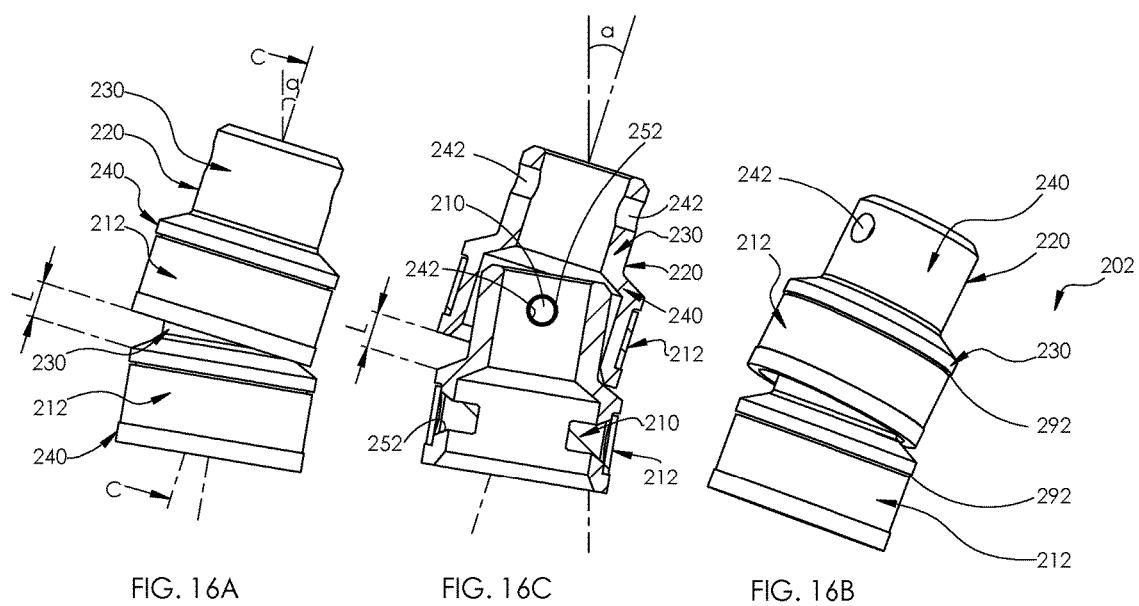
FIGS. 16A, 16B and 16C are perspective view and sectional view simplified illustrations of an embodiment of several subsequent link assemblies of the flexible bone tool of FIG. 10, section being taken along lines C-C in FIG. 16A.

Reference is now made to FIGS. 16A, 16B and 16C, which are perspective view sectional view simplified illustrations of embodiments of several subsequent link assemblies 202 of the flexible bone tool 200, coupled to each other. Link assemblies 202 are shown in FIGS. 16A-C in a bent orientation, the section taken along lines C-C in FIG. 16A.

The embodiment illustrated in FIGS. 16A-16C is depicted in a bent orientation. The link assemblies 202 are positioned at an angle "a" with respect to each other, thus the proximal end of receiving portion 230 of a distal link 220 is angularly displaced with respect to its orientation at rest, as shown in FIG. 15. In some embodiments, angle "a" may be in the range of 2-10 degrees, particularly, the angle of rotation "a" between two subsequent link may be in the range of 5-8 degrees.

Upon bending of the array of link assemblies 202, an axial gap extending over a distance L is created between at least a portion of the circumferences of the adjoined link assemblies 202. Optionally, the extent of the distance L is affected by one or more of: the number of apertures 242 and 252 and corresponding connecting pins 210 coupling the links together; a volume within the receiving link that remains unoccupied by the engaging portion 240, enabling movement of the engaging portion 240 inside the receiving recess.

In some embodiments, one or more dimensions of a link are selected to provide for a certain bending radii range of a tubular body comprising a plurality of links. Optionally, the extent of the bending radius is determined by link dimensions such as: a length of the engaging portion 240 of link 220; an outer diameter of the engaging portion 240 of link 220 and the inner diameter of the receiving portion 230 of the receiving link 220. In some embodiments, a more flexible tubular body which is configured to bend into smaller bending radii can be provided by one or more of: increasing the length dimension; decreasing the outer diameter dimension and increasing the inner diameter dimension. Optionally, selecting the link dimensions for example as described would result in a larger space remaining unoccupied between two subsequent links, so that during bending the links will be more free to rotate.

Figure 17:
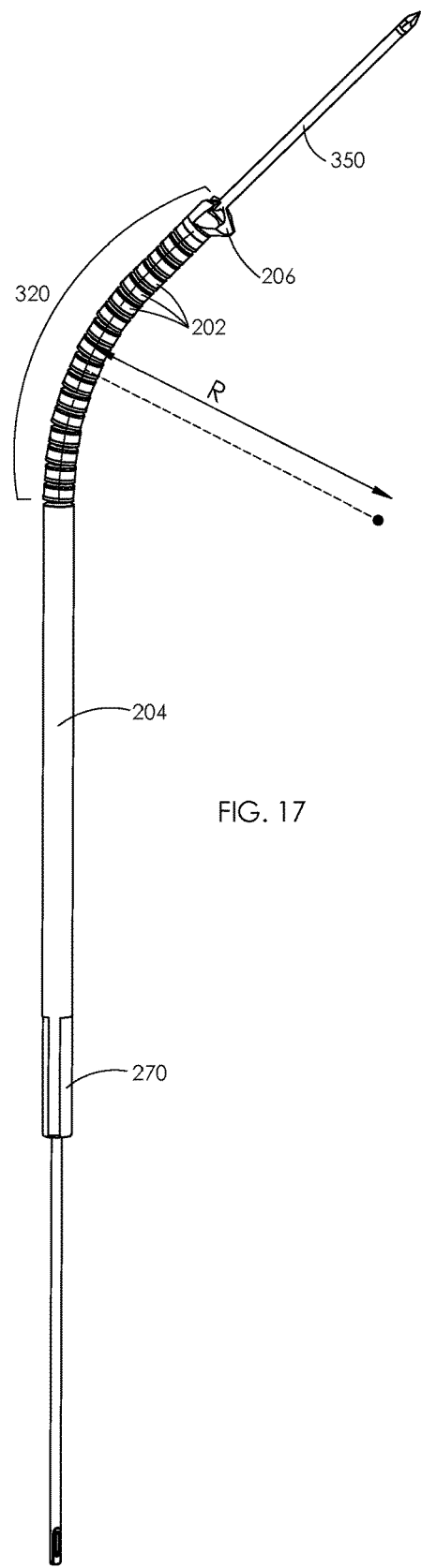
FIG. 17 is a simplified pictorial illustration of an embodiment of the flexible bone tool of FIG. 10 mounted over a guide pin.
Figure 18A:
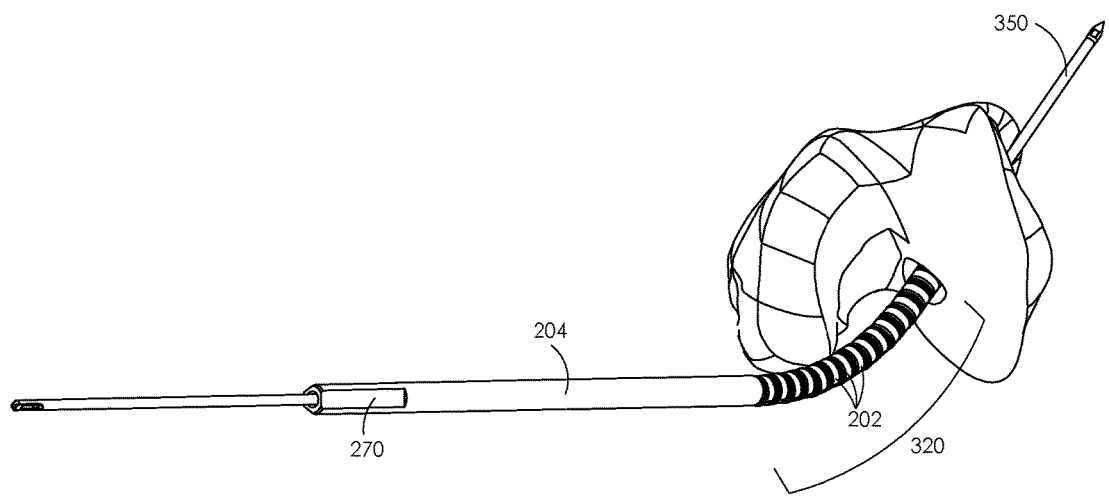
FIGS. 18A and 18B are simplified respective pictorial and sectional views of an embodiment of the flexible bone tool of FIG. 10 mounted over a guide pin, shown in a bent orientation within a bone of a patient.
Figure 18B:
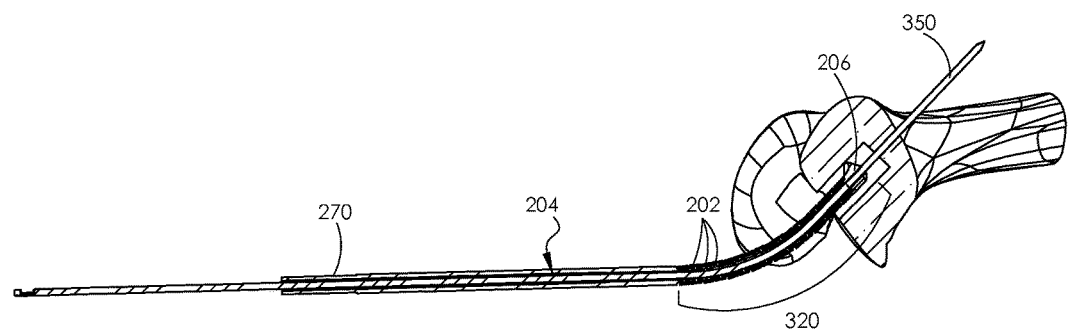

Reference is now made to FIG. 17, which is a side view simplified illustration of the an exemplary embodiment of flexible bone tool 200 mounted over a guide pin, shown in the bent orientation and to FIGS. 18A & 18B, which are perspective view and sectional view simplified illustrations of exemplary embodiments of the flexible bone tool 200 mounted over a guide pin, shown in the bent orientation within a bone of a patient.

As shown in the embodiment depicted in FIG. 17 the array of link assemblies 202, which are securely retained together forms the flexible bone tool 200 having a tubular body 320, a distal portion of which includes the cutting head 206 and a proximal portion of which includes the shaft 204. Flexible bone tool 200 can be threaded over a guide pin 350, protruding from the distal end of the tool 200. The shaft or proximal holding portion 204 includes proximal gripping end 270, which is shaped and/or sized to be engaged by a drill and/or other tool.

In some embodiments, tool 200 is structured to follow a path defined by guide pin 350, for example being a curved and/or straight path. In some embodiments, tubular body 320 is configured to bend into a bending radius R. Optionally, bending radius R can be as small as, for example, 50 mm, 30 mm, 20 mm or intermediate, larger or smaller radii. In some embodiments, the ability of the tubular body to flex to comply with the guide pin curvature is contributed to by the relative angular orientation between the link assemblies 202. Optionally, in some embodiments, during application of rotary motion to the tool (e.g. during drilling), the links would "return" to be aligned with the guide pin path every fraction of the turn which is determined by the angular orientation between consecutive link assemblies 202. For example, in a 90 degree axially rotated orientation between adjacent links, the links would "return" to the defined path every quarter of a turn. Optionally, the rotational orientation of the links reduces a discretization effect during rotation, which may be caused due the rigid links, resulting in a non-continuous rotation. Optionally, reducing the angle between the rotationally oriented adjacent links allows for smoother, substantially continuous rotation of the tubular body of the tool.

In some embodiments, an outer diameter of the tubular body 320 ranges between, for example, 2-10 mm, 4-6.5 mm, 5-20 mm, or intermediate, larger or smaller diameters. Optionally, the tool 200 is configured to form a bore or to ream an existing bore in a bone to similar diameters.

In some embodiments, the tool 200 is advanced along a curved path inside the bone. Optionally, the tool follows a path defined by guide pin 350 as long as the bending radius of the tubular body is compatible with the bending radius of the guide wire. Additionally or alternatively, the tool 200 is advanced along a straight path.

In some embodiments, the tubular body is advanced a certain depth into the bone relative to the surface of the bone, for example a depth ranging between 1 mm to 5 cm. Optionally, the tubular body is advanced to cross through the bone, for example such that cutting head 206 exits a face of the bone which opposes the face through which the tool was inserted.

In some embodiments, the tool is rotated around its axis to advance it into the bone. Optionally, rotary motion is applied by coupling a drill to the head of the proximal gripping end 270. In some embodiments, torque applied onto a proximal end of the tool is transferred by the connected link assemblies to a distal end of the tool 200. In some embodiments, the tool is configured to transfer torque within the range of, for example, 3 N*cm to 5 N*cm, such as 3.2, 4.5, 4.8 N*cm or intermediate, higher or lower values.

In some embodiments, for example when the flexible bone tool is used for drilling a bore in the bone, the tubular body may comprise a flexible core, for example made of Nitinol, stainless steel. Optionally, the core is selected to be flexible enough to allow bending of the tubular body, yet rigid enough to support the links during drilling when the tubular body needs to withstand relatively strong forces from the bone tissue in order to penetrate the bone.

In some embodiments, the flexible bone tool is introduced over the guide pin 350. Optionally, the guide pin 350 defines a curved path leading the flexible bone tool to the bone. Alternatively, the guide pin defines a substantially linear path leading to the bone. In some procedures, it is necessary or preferable to access the bone by following a curved path, (i.e. rather than directly accessing the bone), for example due the anatomy of the treated area. In some procedures, the targeted bone is approached at a certain angle. A flexible tool 200 as described herein may be particularly useful in such procedures, owing to the articulation ability of the tubular body.

In some embodiments, each link is configured to have a degree of freedom to move or pivot in respect to a coupled preceding or following link. The freedom to articulate is limited in some embodiments to pivot between 2-10 degrees in respect to at least one of a preceding or following subsequent links. However, though the maximum degree of pivot angle may in some embodiments remain constant between links, the cumulative effect along the length of a plurality of links results in a bending radius R of the flexible tubular portion 152 of the flexible bone tool 150 between 20 and 80 mm.

In some embodiments, a change in the degree of pivot freedom between consecutive links results in a cumulative bending effect along the full length of the flexible portion of flexible tool 150 affecting the overall bending radius of the tool.

In some cases, the circumferential contact area between the link assembly increases when the distal cutting head 206 of the tool 200 contacts the bone, and the links are axially approximated towards each other. An increased circumferential contact area may provide an advantage during drilling, for example, since the increased contact would contribute to dispersing the load and thereby reduce the load acting on the connecting pins 210 that hold the links together.

In some embodiments, the flexible bone tool is advanced into the bone of a patient. In some embodiments, advancing the tool comprises axially rotating the tubular body, for example by coupling a drill to the proximal holding portion of the tool. Optionally, at least a portion of the tubular body of the tool is advanced into a pre-formed bore in the bone, and widens a diameter of the bore upon advancement. Alternatively, the tool produces the bore. In some embodiments, the snap-fit connection between the plurality of links of the tubular body is strong enough to withstand resisting forces of the bone, while allowing transmission of force such as torque between the links, for example from the proximal holding portion to the distal head.

A method for example as described herein may be especially advantageous in arthroscopic procedures, and particularly useful in Anterior Cruciate Ligament Reconstruction procedures, in which a bore is formed in the femoral bone. In some cases, the bone is approached at a certain angle for forming the bore. Optionally, a flexible bone tool in accordance with some embodiments is introduced to the femoral bone, (optionally over a bent guide wire that was used for creating an initial bore in the bone), and functions as a reamer for widening the initial bore to produce a tunnel for receiving a graft. Optionally, the tool is introduced along a curved path to meet the bone at a desired location.

Figure 19:
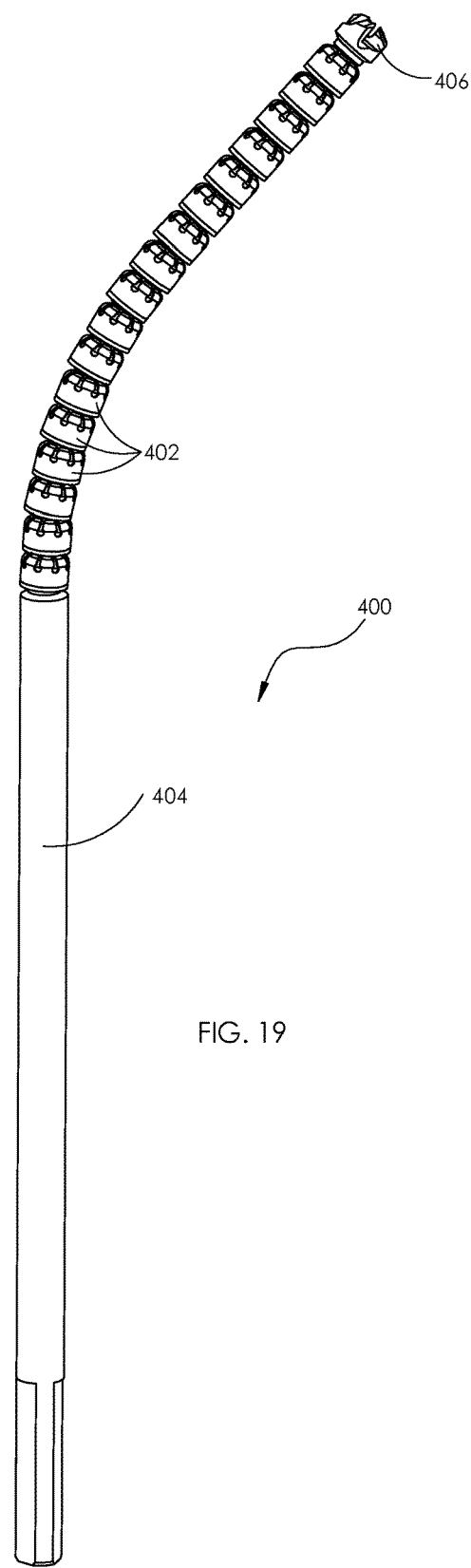
FIG. 19 is a simplified pictorial illustration of an assembled flexible bone tool in accordance with yet another embodiment of the present invention.
Figure 20:
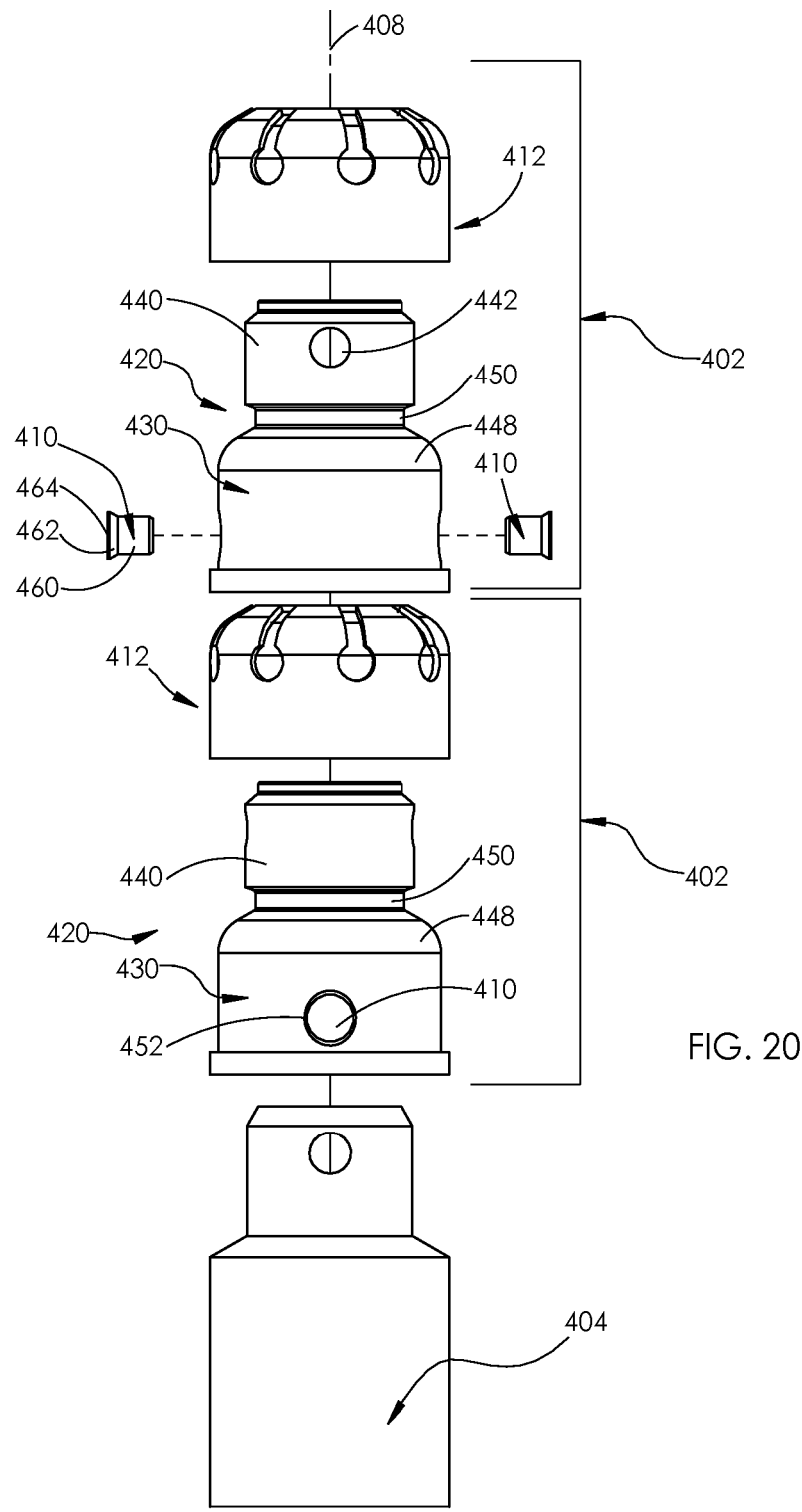
FIG. 20 is a simplified partial exploded illustration of link structure of an embodiment of the flexible bone tool of FIG. 19.

In some embodiments, a user selects a cutting head suitable for performing a desired function (e.g. penetrating a bone to produce a bore, widening an existing bore, and/or other functions), and assembles the head onto the tool 200. Reference is now made to FIG. 19, which is a perspective view simplified illustration of an assembled flexible bone tool, constructed and operative in accordance with an embodiment of the invention and to FIG. 20, which is a simplified partial exploded illustration of link structure of the flexible bone tool of FIG. 19.

As illustrated in FIG. 19, a flexible bone tool 400 comprises a plurality of interconnected link assemblies 402. In some embodiments, the flexible bone tool 400 includes a shaft or proximal holding portion 404 at its proximal end, a plurality of interconnected link assemblies 402, adapted to be pivotably displaced relative to each other and a cutting head 406 at its distal end.

In some embodiments the link assemblies 402 are arranged along a common longitudinal axis 408 at rest. In some embodiments, the interconnected link assemblies define a substantially tubular, bendable body. In some embodiments, the bone tool comprises a cutting head configured at a distal end of the tubular body. Optionally, the cutting head is shaped and/or sized to cut a bore in the bone, allowing the tool to function as a drill bit. Additionally or alternatively, the cutting head is shaped and/or sized to widen an existing bore in the bone, for example when rotary motion is applied to the tool, for example to a proximal head portion of the tool, allowing the tool to function as a reamer. In some embodiments, the bone tool comprises a holding portion configured proximally to the tubular body. The proximal holding portion may be engaged by a user, e.g., a physician, and/or by an additional tool, e.g., a drill. In some embodiments, the tubular body and optionally the proximal holding portion are cannulated. Optionally, the cannulated tool is delivered over a guide wire, guide pin, suture and/or other elongated elements that can fit within and/or be passed through the cannulation.

In some embodiments, a guide wire is introduced to the targeted bone. Optionally, an initial bore is drilled in the bone, for example by advancing the guide wire into the bone, such as with the aid of a drill. In some embodiments, at least a portion of the guide wire is bent into an arch or other curved profile. Optionally, the guide wire is bent into a selected curvature once at least a part of it (e.g. a distal end) has been anchored to the targeted bone.

Each of the link assemblies 402 is configured to be connected to a subsequent, more distal link assembly 402 by means of one or more connecting pins 410 and one or more fixators 412. Each link assembly 402 comprises a link 420, having a receiving portion 430 and an engaging portion 440, configured distally to the receiving portion 430 to be received within a receiving portion 430 of the subsequent link 420.

In some embodiments, engaging portion 440 is generally cylindrical and has two diametrically opposed apertures 442. Alternatively and optionally, engaging portion 440 defines a different outer profile, such as hexagonal, oval, and/or other outer profile configured to be received within the receiving portion 430 of the subsequent link.

In some embodiments, receiving portion 430 comprises a generally cylindrical outer profile with a generally rounded inwardly curved distal end 448, and an annular circumferential neck portion 450 between the receiving portion 430 and the engaging portion 440 of link 420. In some embodiments, a wall of receiving portion 430 and/or the engaging portion 440 comprises two diametrically opposed apertures 452 formed therewithin. Alternatively and optionally, receiving portion 430 defines a different outer profile, such as hexagonal, oval, and/or other outer profile configured to be received within the corresponding engaging portion 440 of the subsequent link.

In some embodiments, the outer diameter of engaging portion 440 of one link 420 is of a generally smaller outer diameter than an inner diameter of the receiving portion 430 of subsequent link 420, so as to fit within the receiving portion 430.

In some embodiments, the inner diameter of receiving portion 430 is generally larger than an outer diameter of the engaging portion 440 of the proximal link 420, so as to receive the engaging portion 440 therein.

In some embodiments, apertures 442 are positioned at an angle of typically 90 degrees with respect to apertures 452.

In some embodiments, each subsequent link 420 is positioned and rotated at an angle e.g., of 90 degrees with respect to a preceding or following consecutive link 420, such that apertures 442 of a first link 420 are aligned with apertures 452 of the second link 420.

In some embodiments, connecting pins 410 include a generally cylindrical portion 460 and a generally outwardly tapered portion 462, defining an outwardly facing surface 464.

In some embodiments, each link comprises a plurality of apertures 442 and 452 and connecting pins 410, for example 2, 3, 4, 5, 6, 10 or intermediate, larger or smaller number of extensions/pins. Optionally, links of a single tool comprise different numbers of extensions/pins. Optionally, the number of extensions/pins determines the extent of movement of the links relative to each other. For example, a single aperture may provide for a higher degree of freedom of movement relative to a larger number of apertures, for example movement in the axial and/or radial directions.

In some embodiments, the links are formed of a metal material, such as, for example, stainless steel. Additionally or alternatively and optionally, the links are formed of a biocompatible plastic, such as, for example, polycarbonate and/or isoplast.

In some embodiments, at least one link and/or at least the tubular body and/or cutting head are disposable.

In some embodiments, the magnitude of torque transferred by the links is sufficient for drilling into the bone tissue, for example ranging between 3 N*cm-15 N*cm. Optionally, the tubular body is configured to transfer a magnitude of torque ranging between 1 N*cm to 150 N*cm, such as 5-20 N*cm, 10-40 N*cm, 50-100 N*cm. In some embodiments, the matching non-circular geometries of the engaging portion and the inner lumen of the receiving portion are selected to allow axial rotation of the link assemblies 402 relative to each other only to an extent in which sufficient torque can still be transferred between the links. In some embodiments, shaft 404 of flexible bone tool 400 is substantially identical to shaft 204 shown in FIG. 10. In some embodiments, shaft 404 of flexible bone tool 400 is similar to shaft 204 shown in FIG. 10.

Figure 21A:
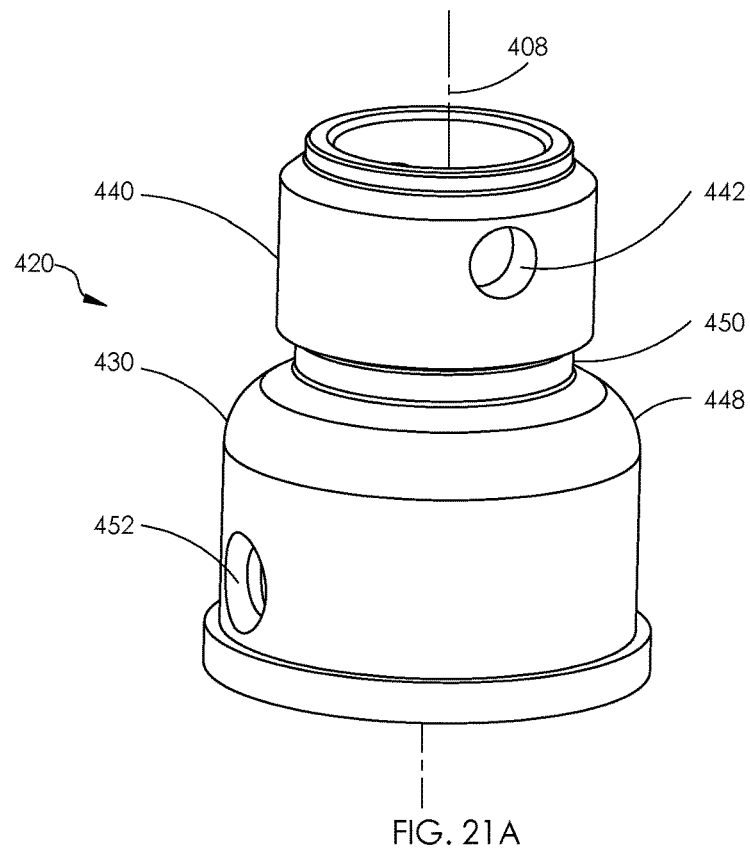
FIGS. 21A and 21B are perspective view and sectional view simplified illustrations of an embodiment of a link of the flexible bone tool of FIG. 19.
Figure 21B:
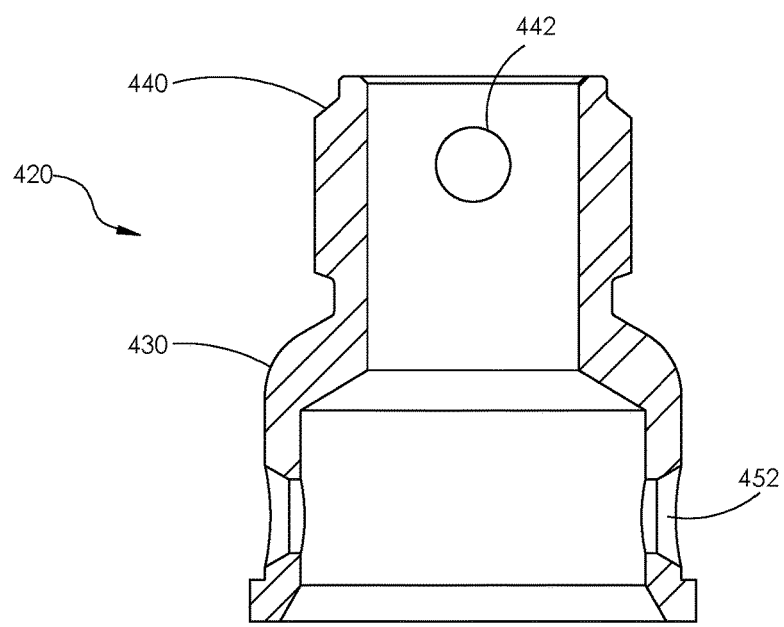

Reference is now made to FIGS. 21A & 21B, which are perspective view and sectional view simplified illustrations of a single link 420 of the flexible bone tool 400. In some embodiments, a link 420 is made of a metallic material e.g., stainless steel and is manufactured by means of deep drawing.

As described in detail herein, the link 420 comprises receiving portion 430 sized and fitted to receive an engaging portion 440 of a subsequent link 420.

In some embodiments, engaging portion 440 is generally cylindrical and has two diametrically opposed apertures 442 extending along an axis which is transversely disposed with respect to longitudinal axis 408. Alternatively, engaging portion 440 defines a different outer profile, such as hexagonal, oval, and/or other outer profile configured to be received within the receiving portion 430 of the subsequent link.

In some embodiments, receiving portion 430 is of a generally cylindrical outer profile, having rounded distal end 448 and forming annular neck portion 450 between the receiving portion 430 and the engaging portion 440. Typically, two diametrically opposed apertures 452 are formed in receiving portion 430 and extending along an axis which is transversely oriented with respect to longitudinal axis 408. Alternatively, receiving portion 430 defines a different outer profile, such as hexagonal, oval, and/or other outer profile configured to be received within the corresponding engaging portion 440 of the subsequent link.

Apertures 452 are positioned on a plane which is generally perpendicular to the plane on which apertures 442 are positioned.

In some embodiments, the outer profile of engaging portion 440 of a first link 420 is of a generally smaller outer diameter than an inner diameter of a receiving portion 430 of subsequent link 420, so as to fit within the receiving portion 430.

In some embodiments, the inner diameter of receiving portion 430 is generally larger than an outer diameter of the engaging portion 440 of the proximal link 420, so as to receive the engaging portion 440 therein.

In some embodiments, apertures 452 are positioned at an angle of typically 90 degrees with respect to apertures 442.

In some embodiments, the diameter of the single link 420 is within the range of 2-6.5 mm and the length of the single link 420 is within the range of 4-8 mm.

Figure 22A:
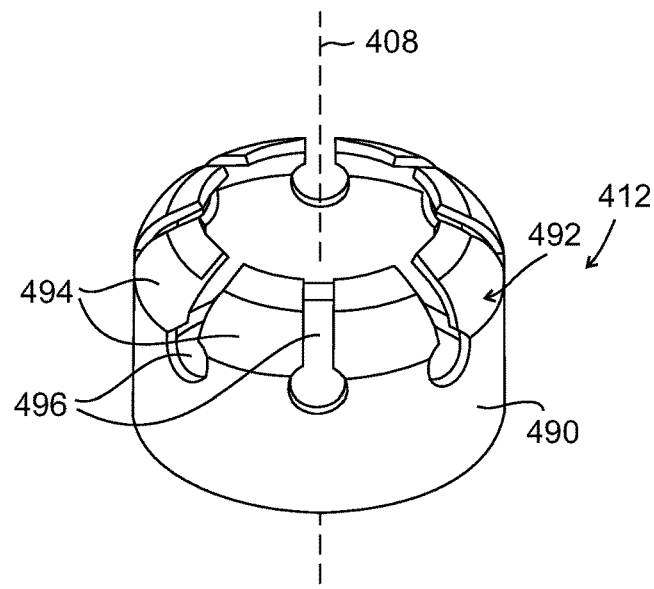
FIGS. 22A and 22B are simplified pictorial illustration of a fixation element of the flexible bone tool of FIG. 19.
Figure 22B:
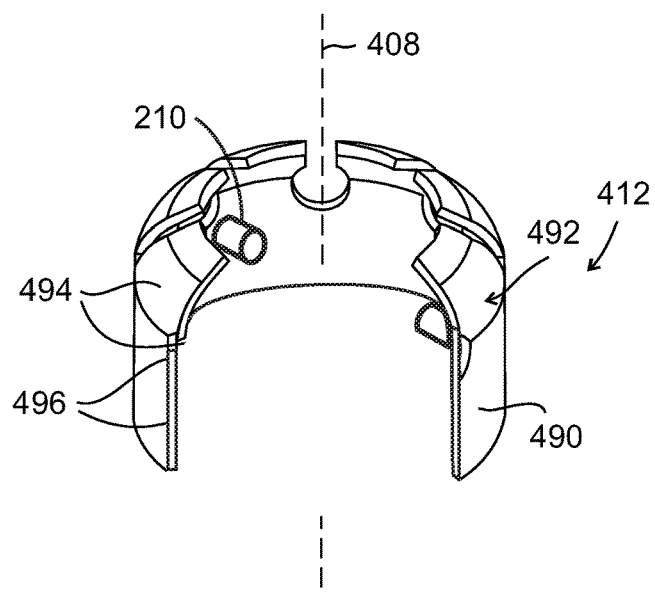

Reference is now made to FIGS. 22A and 22B, which are simplified pictorial illustration of exemplary embodiments of a fixation element 412, of the flexible bone tool 400.

In some embodiments, fixation element 412/414 is an integrally made element having a cylindrical or semi-circular proximal portion 490 and a notional dome geometry generally rounded inwardly curved or extending distal portion 492 having a plurality of mutually separated finger-like projections 494, defining gaps 496 therebetween. Gaps 496 enable the fixation element 412 to deform resiliently upon application of stress.

As shown in the embodiment of FIG. 22B, fixation element 414 has semi-circular geometry comprising a gap 450 and integrally coupled one or more pins 410. Due to their resilient qualities, fixation elements 412/414 comprise a snap-fit attachment to a corresponding link 420.

Figure 23:
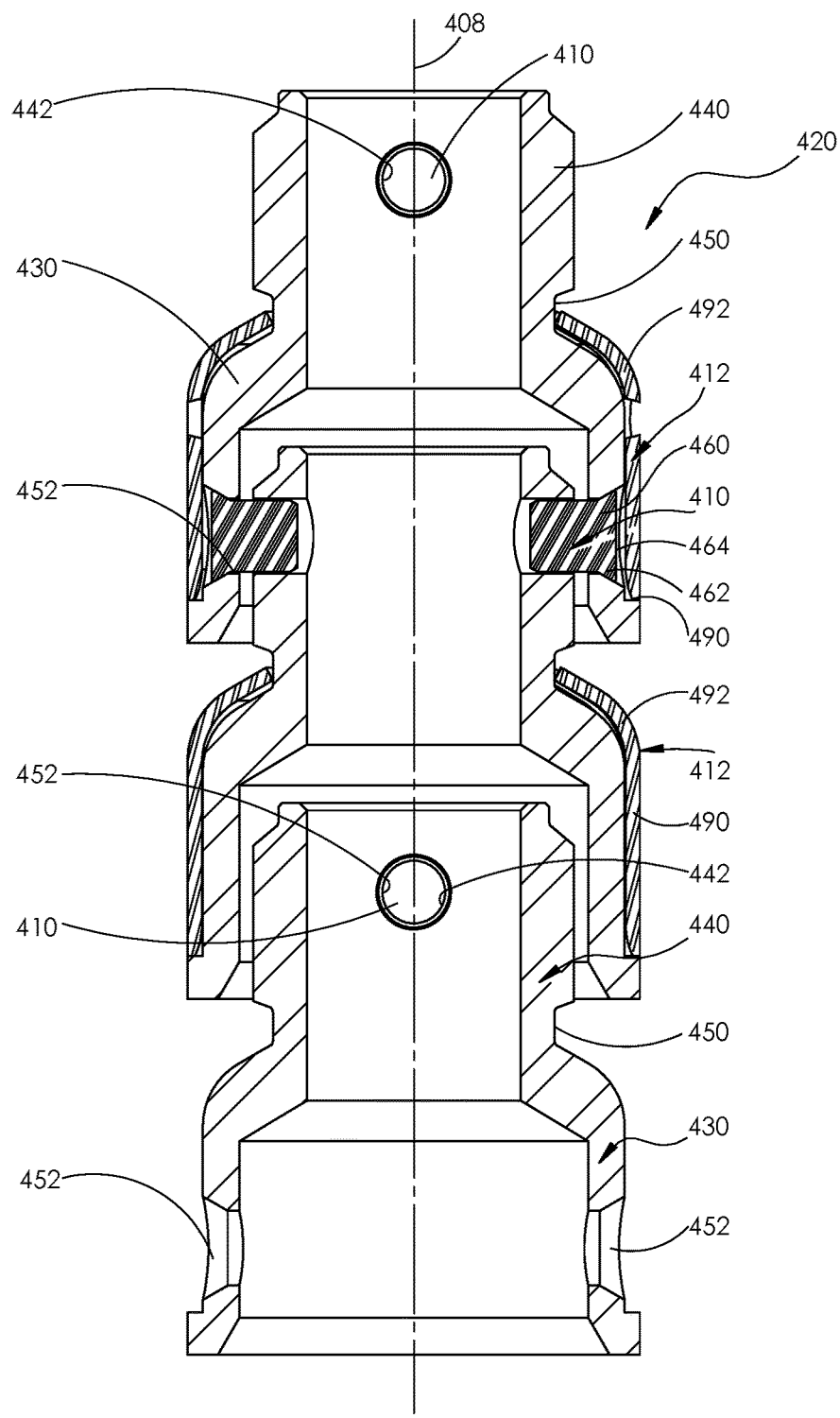
FIG. 23 is a partial sectional view simplified illustration taken along several subsequent links of the flexible bone tool of FIG. 19.

Reference is now made to FIG. 23, which is a partial sectional view simplified illustration of a flexible segment of the flexible bone tool in accordance with some embodiments of the invention taken along several subsequent link assemblies 402 of the flexible bone tool 400, coupled to each other, at rest orientation.

As shown in the exemplary embodiment of FIG. 23, a proximal link 420 and a subsequent distal receiving link 420 are axially rotated perpendicularly in respect to each other. The apertures 452 of the proximal link 420, at a cross section, are shown to extend on a plane which is perpendicular to the plane of the cross section of apertures 442 of distal link 420.

The links 420 are coupled to each other using connecting pins 410. Apertures 442 of a proximal link 420 are aligned with apertures 452 of a distal link 420 and the connecting pins 410 are inserted through both apertures 442 and 452 and secure the two links together, while providing at least rotational or pivotal degree of freedom, as particularly seen further in FIGS. 24A-24C.

It is a particular feature of an embodiment of the present invention that the connecting pins 410 cannot be fully inserted into the interior of a link 420, due to the fact that the connecting pins 410 have outwardly tapered portion 462. It is a further particular feature of an embodiment of the present invention that fixation element 412 is mounted onto receiving portion 430 of each link 420, such that inwardly extending distal portion 492 is retained on neck portion 450 of each link 420. The fixation element 412 engages the outwardly facing surface 464 of connecting pins, thus preventing the connecting pins 410 from falling out of apertures 442 and 452, and thus the connecting pins 410 are securely held within the links 420 and securely retain the plurality of links 420 together. It is noted that it is possible mounting the fixation element 412 onto the link 420 due to its spring characteristics provided by gaps 496.

Figure 24A:
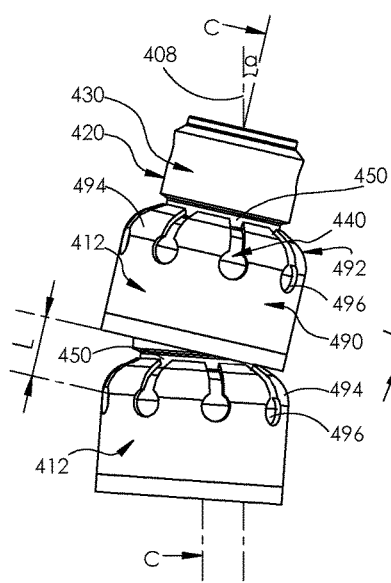
FIGS. 24A, 24B and 24C are perspective view and sectional view simplified illustrations of several subsequent links of the flexible bone tool of FIG. 19, the section taken along lines C-C in FIG. 24A.
Figure 24C:
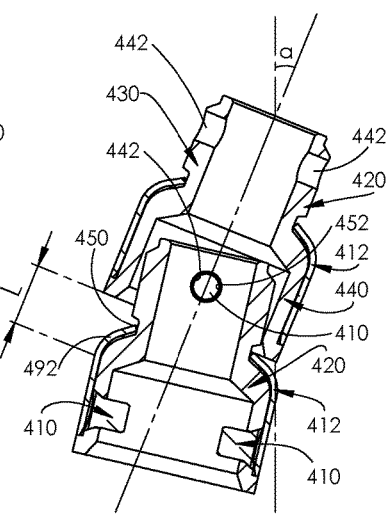
Figure 24B:
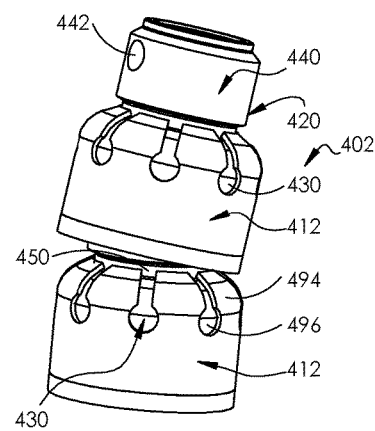

Reference is now made to FIGS. 24A-24C, which are simplified respective two different pictorial and a sectional view of several subsequent link assemblies 402 of the flexible bone tool 400 of FIG. 19, coupled to each other, the link assemblies 402 are shown in a bent orientation, section being taken along lines C-C in FIG. 24A.

It is particularly seen in FIGS. 24A-24C that in a bent orientation, the link assemblies 402 are positioned at an angle "a" with respect to each other, thus the proximal end of receiving portion 430 of a distal link 420 is angularly displaced with respect to its orientation at rest, as shown in FIG. 23. In some embodiments, angle "a" may be in the range of 2-10 degrees, particularly, the angle of rotation "a" between two subsequent link may be in the range of 5-8 degrees.

Upon bending of the array of link assemblies 402, an axial gap extending over a distance L is created between at least a portion of the circumferences of the adjoined link assemblies 402. Optionally, the extent of the distance L is affected by one or more of: the number of apertures 442 and 452 and corresponding connecting pins 410 coupling the links together; a volume within the receiving link that remains unoccupied by the engaging portion 440, enabling movement of the engaging portion 440 inside the receiving recess.

In some embodiments, one or more dimensions of a link are selected to provide for a certain bending radii range of a tubular body comprising a plurality of links. Optionally, the extent of the bending radius is determined by link dimensions such as: a length of the engaging portion 440 of link 420; an outer diameter of the engaging portion 440 of link 420 and the inner diameter of the receiving portion 430 of the receiving link 420. In some embodiments, a more flexible tubular body which is configured to bend into smaller bending radii can be provided by one or more of: increasing the length dimension; decreasing the outer diameter dimension and increasing the inner diameter dimension. Optionally, selecting the link dimensions for example as described would result in a larger space remaining unoccupied between two subsequent links, so that during bending the links will be freer to rotate.

Figure 25:
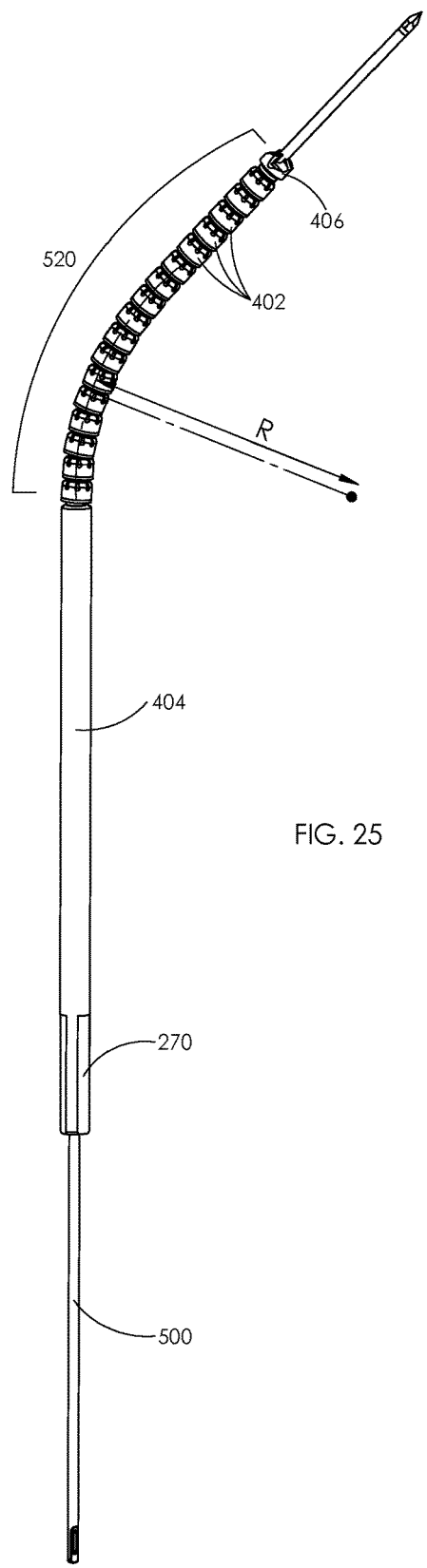
FIG. 25 is a perspective view simplified illustration of the flexible bone tool of FIG. 19 mounted over a guide pin in the bent orientation.
Figure 26A:
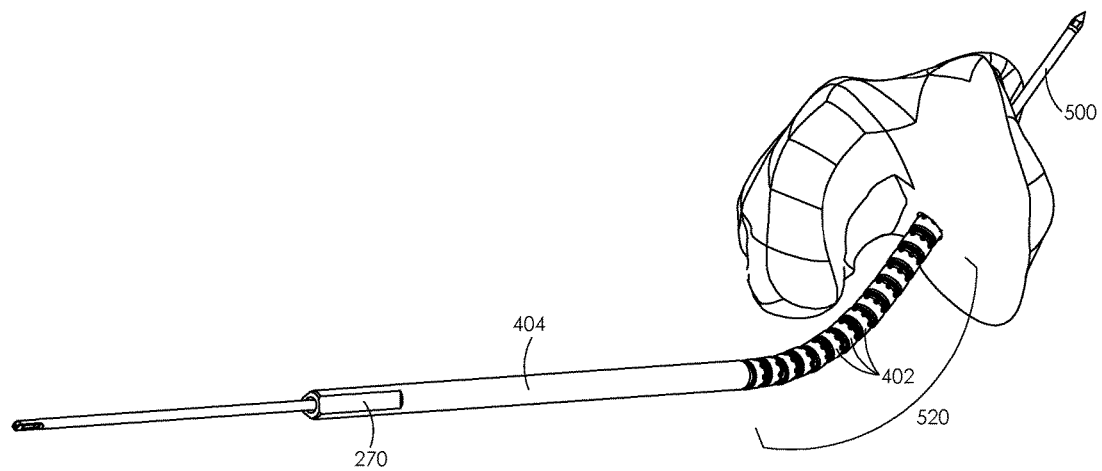
FIGS. 26A and 26B are simplified perspective view and sectional view simplified illustrations of the flexible bone tool of FIG. 19 mounted over a guide pin, shown in the bent orientation within a bone of a patient.
Figure 26B:
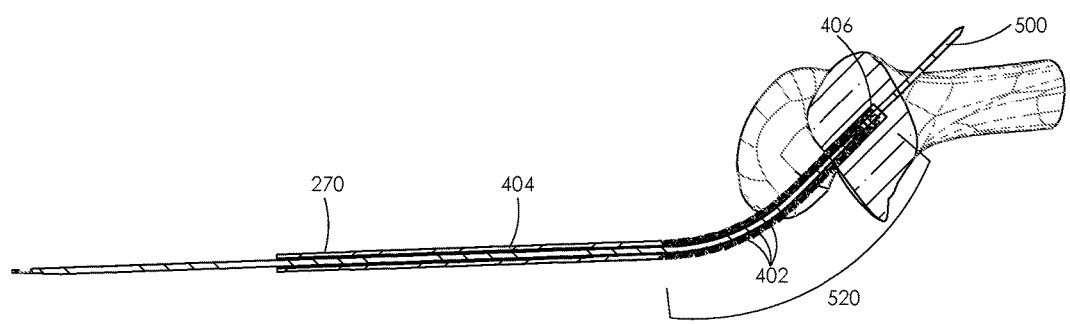

Reference is now made to FIG. 25, which is a side view simplified illustration of the flexible bone tool 400 mounted over a guide pin, shown in the bent orientation and to FIGS. 26A & 26B, which are perspective view and sectional views simplified illustrations of embodiments of the flexible bone tool 400 mounted over a guide pin, shown in the bent orientation within a bone of a patient.

As shown in the exemplary embodiment depicted in FIG. 25 the array of link assemblies 402, which are securely retained together forms the flexible bone tool 400 having a tubular body 520, a distal portion of which includes the cutting head 406 and a proximal portion of which includes the shaft 404. Flexible bone tool 400 can be threaded over a guide pin 500, protruding from the distal end of the tool 400. The shaft 404 includes proximal gripping end 270, which is shaped and/or sized to be engaged by a drill and/or other tool.

In some embodiments, tool 400 is structured to follow a path defined by guide pin 500, for example being a curved and/or straight path. In some embodiments, tubular body 520 is configured to bend into a bending radius R. Optionally, bending radius R can be as small as, for example, 50 mm, 30 mm, 20 mm or intermediate, larger or smaller radii.

In some embodiments, the ability of the tubular body to flex to comply with the guide pin curvature is contributed to by the angular orientation between the link assemblies 402. Optionally, during application of rotary motion to the tool (e.g. during drilling), the links would "return" to be aligned with the guide pin path every fraction of the turn which is determined by the angular orientation between the link assemblies. In an example, in a 90 degree orientation between adjacent links, the links would "return" to the defined path every quarter of a turn. Optionally, the rotational orientation of the links reduces a discretization effect during rotation, which may be caused due the rigid links, resulting in a non-continuous rotation. Optionally, reducing the angle between the rotationally oriented adjacent links allows for smoother, substantially continuous rotation of the tubular body of the tool.

In some embodiments, an outer diameter of the tubular body 520 ranges between, for example, 2-10 mm, 4-6.5 mm, 5-20 mm, or intermediate, larger or smaller diameters. Optionally, the tool 400 is configured to form a bore or to ream an existing bore in a bone to similar diameters.

In some embodiments, the tool 400 is advanced along a curved path inside the bone. Optionally, the tool follows a path defined by guide pin 500 as long as the bending radius of the tubular body is compatible with the bending radius of the guide wire. Additionally or alternatively, the tool 400 is advanced along a straight path.

In some embodiments, the tubular body is advanced a certain depth into the bone relative to the surface of the bone, for example a depth ranging between 1 mm to 5 cm. Optionally, the tubular body is advanced to cross through the bone, for example such that cutting head 406 exits a face of the bone which opposes the face through which the tool was inserted.

In some embodiments, the tool is rotated around its axis to advance it into the bone. Optionally, rotary motion is applied by coupling a drill to the head of the proximal gripping end 270. In some embodiments, torque applied onto a proximal end of the tool is transferred by the connected link assemblies to a distal end of the tool 400. In some embodiments, the tool is configured to transfer torque within the range of, for example, 3 N*cm to 5 N*cm, such as 3.2, 4.5, 4.8 N*cm or intermediate, higher or lower values.

In some embodiments, for example when the flexible bone tool is used for drilling a bore in the bone, the tubular body may comprise a flexible core, for example made of Nitinol, stainless steel. Optionally, the core is selected to be flexible enough to allow bending of the tubular body, yet rigid enough to support the links during drilling when the tubular body needs to withstand relatively strong forces from the bone tissue in order to penetrate the bone.

In some embodiments, the flexible bone tool is introduced over the guide pin 500. Optionally, the guide pin 500 defines a curved path leading the flexible bone tool to the bone. Alternatively, the guide pin defines a substantially linear path leading to the bone. In some procedures, it is necessary or preferable to access the bone by following a curved path, (i.e. rather than directly accessing the bone), for example due the anatomy of the treated area. In some procedures, the targeted bone is approached at a certain angle. A flexible tool 400 as described herein may be particularly useful in such procedures, owing to the articulation ability of the tubular body.

In some cases, the circumferential contact area between the link assembly increases when the distal cutting head 406 of the tool 400 contacts the bone, and the links are axially approximated towards each other. An increased circumferential contact area may provide an advantage during drilling, for example, since the increased contact would contribute to dispersing the load and thereby reduce the load acting on the connecting pins 410 that hold the links together.

In some embodiments, the flexible bone tool is advanced into the bone of a patient. In some embodiments, advancing the tool comprises axially rotating the tubular body, for example by coupling a drill to the proximal holding portion of the tool. Optionally, at least a portion of the tubular body of the tool is advanced into a pre-formed bore in the bone, and widens a diameter of the bore upon advancement. Alternatively, the tool produces the bore. In some embodiments, the snap-fit connection between the plurality of links of the tubular body is strong enough to withstand resisting forces of the bone, while allowing transmission of force such as torque between the links, for example from the proximal holding portion to the distal head.

A method for example as described herein may be especially advantageous in arthroscopic procedures, and particularly useful in Anterior Cruciate Ligament Reconstruction procedures, in which a bore is formed in the femoral bone. In some cases, the bone is approached at a certain angle for forming the bore. Optionally, a flexible bone tool in accordance with some embodiments is introduced to the femoral bone, (optionally over a bent guide wire that was used for creating an initial bore in the bone), and functions as a reamer for widening the initial bore to produce a tunnel for receiving a graft. Optionally, the tool is introduced along a curved path to meet the bone at a desired location.

Figure 27A:
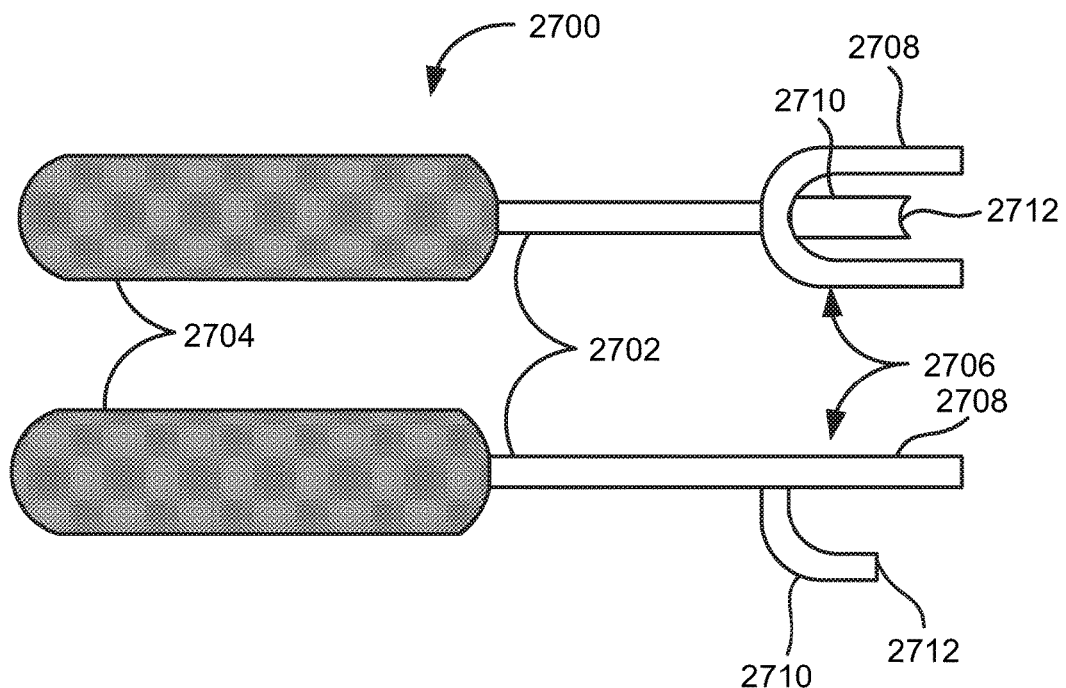
Figure 27B:
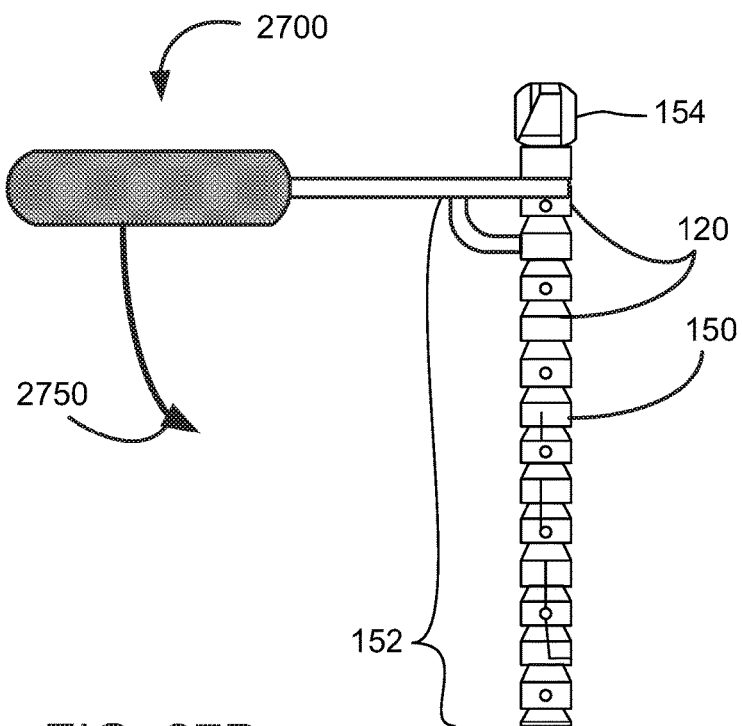

In some embodiments, a user selects a cutting head suitable for performing a desired function (e.g. penetrating a bone to produce a bore, widening an existing bore, and/or other functions), and assembles the head onto the tool 400. Reference is now made to FIGS. 27A and 27B, in which FIG. 27A is a plan view and side view simplified illustration of a link detachment tool in accordance with some embodiments of the invention and FIG. 27B is a side view simplified illustration of implementation of the link detachment tool depicted in FIG. 27A. As shown in the exemplary embodiment shown in FIG. 27A, link detachment tool 2700 comprises a shaft 2702 coupled at a first end to a handle 2704 and at a second end to a detaching end 2706. In some embodiments, detaching end 2706 is pronged and comprises one or more prongs sized and fitted to be inserted between any two consecutive links 120 and/or link assemblies 220 of flexible bone tool 150. In some embodiments, detaching end 2706 comprises two or more prongs 2708 sized and fitted to be inserted between any two consecutive links 120 along at least a portion of a circumference of flexible bone tool 150.

In some embodiments, tool 2700 comprises a cantilevered arm 2710 that extends from shaft 2702 at an angle with respect to a longitudinal axis of shaft 2702.

Figure 28:
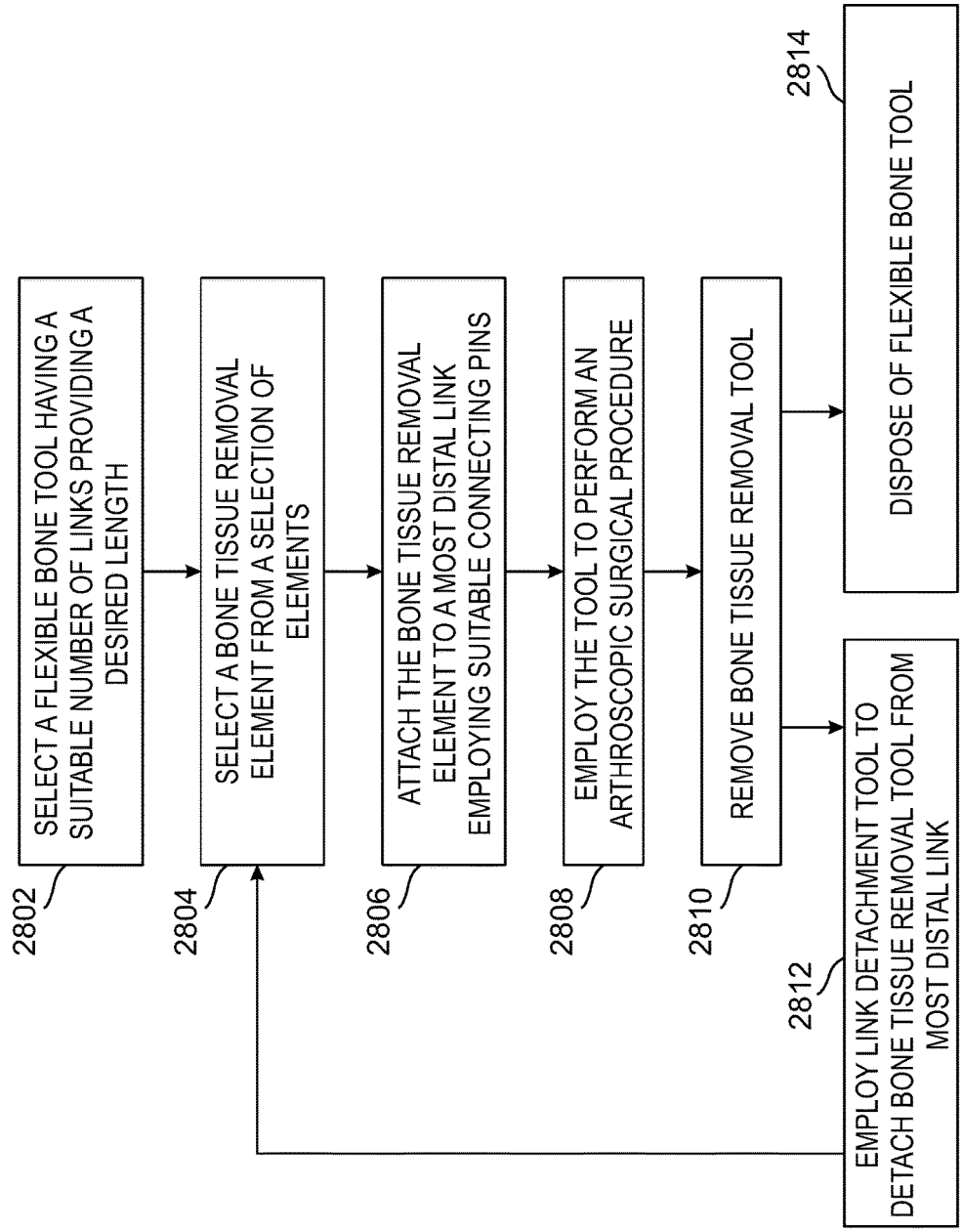
FIG. 28 is a flow chart of a method of use of a flexible bone tool kit for drilling a curved bore in bone.

In the example shown in FIG. 27B, link detachment tool 2700 is applied to flexible bone tool 150 between a bone tissue removal element 154 and a preceding coupled link 120. In some embodiments, an end surface 2712 of cantilevered arm 2710 rests on an outer surface of one or more preceding links 120 and provides leverage to detachment end 2700 when detachment tool 2700 handle 2704 is urged in a direction indicated by arrow 2750. Referring now to FIG. 28, which is a simplified flow chart of a method of using a flexible bone tool kit.

In some embodiments, a flexible bone tool kit comprises at least one of a flexible bone tool having a holding portion, at least one first link attachable distally to the holding portion, at least one second link comprising a tissue removing element attachable to at least one of the holding portion and first link, a plurality of connecting pins and at least one link detachment tool.

In some embodiments and as shown in FIG. 28, which is a method of using a kit comprises at step 2802 selecting a flexible bone tool comprising a suitable number of links providing a desired length in accordance with the procedure to be performed (e.g., arthroscopic procedure). In some embodiments at 2804 selecting a suitable bone tissue removal element e.g., bone cutting element, reamer, drill and any other bone tissue removal and manipulating device and attaching the element to the most distal link of the flexible bone tool employing connecting pins (2806). At 2808 performing the surgical procedure and removing the flexible bone tool once the procedure is terminated (2810). In some embodiments, the flexible bone tool is discarded at this point (2814). In some embodiments, a link detachment tool is used to detach the bone tissue removal element from the distal link 2812 and a same or different bone tissue removal element is attached (2804).

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A flexible bone tool kit for drilling a curved bore in bone comprising:
    at least one flexible bone tool comprising at least one proximal holding portion;
    at least one first link attachable distally to said holding portion, said at least one first link including an engaging portion having an outer diameter;
    at least one second link comprising a tissue removing element attachable to at least one of said holding portion and said first link, said at least one second link including a receiving portion having an inner diameter, wherein said outer diameter is smaller than said inner diameter;
    a plurality of connecting pins; and
    at least one link detachment tool.

2. The kit according to claim 1, wherein said link detachment tool is configured to detach links and/or said link comprising a tissue removing element.

3. A method of using a flexible bone tool kit for drilling a bore in bone comprising:
    selecting at least one flexible bone tool comprising at least one proximal holding portion;
    selecting at least one first link and attaching said at least one first link to said holding portion;
    selecting at least one second link comprising a tissue removing element; and
    attaching said second link to said first link with at least one pin;
    wherein each said at least one second link includes a receiving portion having an inner diameter,
    each said at least one first link including an engaging portion having an outer diameter;
    wherein a said outer diameter of said engaging portion is smaller than a said inner diameter of a said receiving portion, wherein a said receiving portion is sized and fitted to receive a said engaging portion.

4. A flexible bone tool comprising:
    a holding portion;
    a bone tissue removing element, wherein said bone tissue removing element comprises a receiving portion;
    at least one link moveably coupled to said bone tissue removing element and collectively defining a bendable body;
    said at least one link coupled
        a) at a proximal end to the holding portion; and
        b) at a distal end to said bone tissue removing element;
    wherein each of said at least one link and bone tissue removing element has a receiving portion, a wall of which comprises at least one second aperture, each said receiving portion having an inner diameter;
    wherein each of said at least one link has an engaging portion, a wall of which comprises at least a first aperture, each said engaging portion having an outer diameter, wherein said outer diameter of a said engaging portion is smaller than a said inner diameter of a said receiving portion of a subsequent said link;

wherein each said engaging portion has a cross-sectional circumferential geometry corresponding to a cross-sectional circumferential geometry of a subsequent said receiving portion;

wherein each said receiving portion is sized and fitted to receive a said engaging portion such that said first and second apertures are aligned; and wherein said flexible bone tool includes at least one pin sized and fitted to be received by said aligned first and second apertures and to movably couple each said receiving portion and received engaging portion.

5. The flexible bone tool according to claim 4, wherein said at least one link comprises a plurality of links, wherein said links comprise an engaging portion and a receiving portion each comprising at least one pair of diametrically opposed apertures.

6. The flexible bone tool according to claim 5, wherein a first imaginary line connecting a pair of diametrically opposed apertures in a said receiving portion is at an angle in respect to a second imaginary line connecting diametrically opposed apertures in a said engaging portion.

7. The flexible bone tool according to claim 4, wherein said at least one pin stops said engaging portion from being fully inserted inside said receiving portion, forming a gap between an outer surface of said engaging portion and an inner surface of said receiving portion.

8. The flexible bone tool according to claim 7, wherein said gap allows pivotal movement of said engaging portion inside said receiving portion such that said at least one link is operative to pivot 2-10 degrees in respect to said bone tissue removing element.

9. The flexible bone tool according to claim 8, wherein said at least one link comprises a plurality of links, and wherein degrees of pivot along said plurality of links collectively define a bending radius of said tool.

10. The flexible bone tool according to claim 4, wherein said tool comprises at least 7 links and is configured to bend in a bending radius R between 20 and 80 mm.

11. The flexible bone tool according to claim 4, wherein said tool comprises at least 7 links and is configured to bend at an angle between 0 and 180 degrees in respect to the rotational axis of said holding portion.

12. The flexible bone tool according to claim 4, wherein said at least one link comprises a plurality of links each having a receiving portion, and wherein matching geometries of a said engaging portion and a corresponding inner lumen of a consecutive receiving portion are suitable when engaged for transferring torque between the links at a magnitude sufficient for advancing the bone tissue removal element into a bone.

13. The flexible bone tool according to claim 4, wherein said at least one link comprises a plurality of links each having a receiving portion, and wherein matching geometries of a said engaging portion and a corresponding inner lumen of a consecutive receiving portion allow axial rotation of said links relative to each other only to an extent in which sufficient torque can still be transferred between the links.

14. The flexible bone tool according to claim 4, wherein at least a portion of said flexible tool is slidable over at least one of a guide pin and a guide wire.

15. The flexible bone tool according to claim 4, wherein said at least one link comprises a plurality of links, and wherein said coupling comprises a radial interference connection in which at least one pin is received within aligned apertures of two subsequent links.

16. The flexible bone tool according to claim 4, wherein at least one of said bendable body and said holding portion is cannulated.

17. The flexible bone tool according to claim 4, further comprising a fixator.

18. The flexible bone tool according to claim 17, wherein said fixator has one of annular geometry and semicircular geometry.

19. The flexible bone tool according to claim 17, wherein said fixator is resilient and defines one of:
an inwardly facing surface, an outwardly facing surface and a slit, which enables the fixator to deform resiliently upon application of stress; and
a notional dome geometry comprising a plurality of mutually separated finger-like projections.

20. The flexible bone tool according to claim 19, wherein said fixator defines an inwardly facing surface, an outwardly facing surface and a slit, which enables the fixator to deform resiliently upon application of stress, wherein said at least one link comprises a plurality of links each having a receiving portion, and wherein an outer surface of a said receiving portion of a said link comprises a circumferential recess having apertures formed therein, said at least one pin each received by an aperture formed in said recess, wherein said fixator lies along said circumferential recess with said inwardly facing surface engaging an outwardly facing surface of at least one of said pins received in said apertures.

21. The flexible bone tool according to claim 17, wherein said fixator comprises diametrically opposed fixedly attached pins.

22. The flexible bone tool according to claim 4, wherein said at least one link comprises a plurality of links each having a receiving portion, and wherein a bending radius of said bendable body is defined by at least one of:
the number of links comprising said body; and
an outer diameter of said engaging portion of said links, a length of said engaging portion of said links, and an inner diameter of a receiving portion of said links.

23. The flexible bone tool according to claim 4, wherein at least one of said apertures is axially oblong.

24. The flexible bone tool according to claim 23, wherein said flexible tool comprises at least one axial gap between at least two subsequent links that is reducible upon said tool contacting bone.

25. The flexible bone tool according to claim 4, wherein said bone tissue removing element is replaceable.

* * * * *